US007524483B2

(12) United States Patent
Aime et al.

(10) Patent No.: US 7,524,483 B2
(45) Date of Patent: Apr. 28, 2009

(54) RESPONSIVE PARAMAGNETIC MRI CONTRAST AGENTS

(75) Inventors: Silvio Aime, Carignano (IT); Daniela Delli Castelli, Bibiana (IT); Franco Fedeli, Vimodrone (IT); Enzo Terreno, Turin (IT)

(73) Assignee: Bracco Imaging S.p.A., Milan (IT)

( * ) Notice: Subject to any disclaimer, the term of this patent is extended or adjusted under 35 U.S.C. 154(b) by 910 days.

(21) Appl. No.: 10/502,701

(22) PCT Filed: Jan. 27, 2003

(86) PCT No.: PCT/EP03/00796

§ 371 (c)(1),
(2), (4) Date: Jul. 27, 2004

(87) PCT Pub. No.: WO03/063912

PCT Pub. Date: Aug. 7, 2003

(65) Prior Publication Data

US 2005/0191243 A1 Sep. 1, 2005

(30) Foreign Application Priority Data

Jan. 29, 2002 (EP) .................................. 02001178

(51) Int. Cl.
*A61B 5/055* (2006.01)
(52) U.S. Cl. ...................... 424/9.365; 424/9.1; 424/9.3; 424/9.36; 534/15
(58) Field of Classification Search ................ 424/1.11, 424/1.65, 9.1, 9.2, 9.3, 9.32, 9.34, 9.35, 9.36, 424/9.361, 9.362, 9.363, 9.364, 9.365, 9.37; 534/7, 10–16
See application file for complete search history.

(56) References Cited

U.S. PATENT DOCUMENTS 5,190,744 A * 3/1993 Rocklage et al. ........... 424/9.34

FOREIGN PATENT DOCUMENTS

WO WO/0243775 6/2002

OTHER PUBLICATIONS

Zhang et al (J. Am. Chem. Soc., Jan. 26, 2001, vol. 123, No. 7, pp. 1517-1518).*
PCT International Search Report for PCT/EP03/00796 dated May 27, 2003.
PCT International Preliminary Examination Report for PCT/EP03/00796 dated May 10, 2004.
Zhang et al.: "A Novel PH-Sensitive MRI Contrast Agent", Angewandte Chemie. International Edition, vol. 38, No. 21, pp. 3192-3194 (1999).
Aime et al.: "High-resolution NMR and relaxometric studies of Ln(III) complexes of relevance of MRI", Journal of Alloys and Compounds, vol. 225, pp. 274-278 (1995).
Ward et al.: "A new class of contrast agents for MRI based on proton chemical exchange dependent saturation transfer (CEST)", Journal of Magnetic Resonance, vol. 143, No. 1, pp. 79-87 (2000).
Ward et al.: "Determination of PH Using Water Protons and Chemical Exchange Dependent Saturation Transfer (CEST)", Magnetic Resonance in Medicine, vol. 44, No. 5, pp. 799-802 (2000).
Balaban et al.: "Magnetization Transfer Contrast in Magnetic Resonance Imaging", Magnetic Resonance Quarterly, vol. 8, No. 2, pp. 116-137 (1992).

* cited by examiner

*Primary Examiner*—D. L Jones
(74) *Attorney, Agent, or Firm*—Kramer Levin Naftalis & Frankel LLP

(57) ABSTRACT

A method is claimed based on CEST procedure for the in vivo or in vitro determination of physical or chemical parameters which includes the use of a responsive paramagnetic CEST contrast agent.

14 Claims, 9 Drawing Sheets

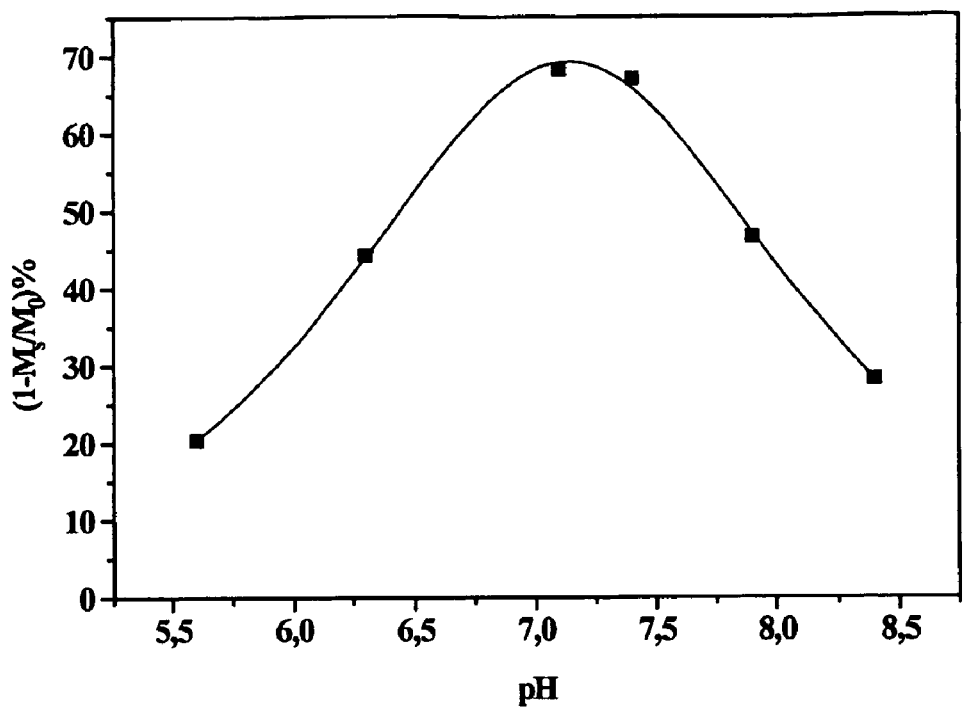
Figure 6
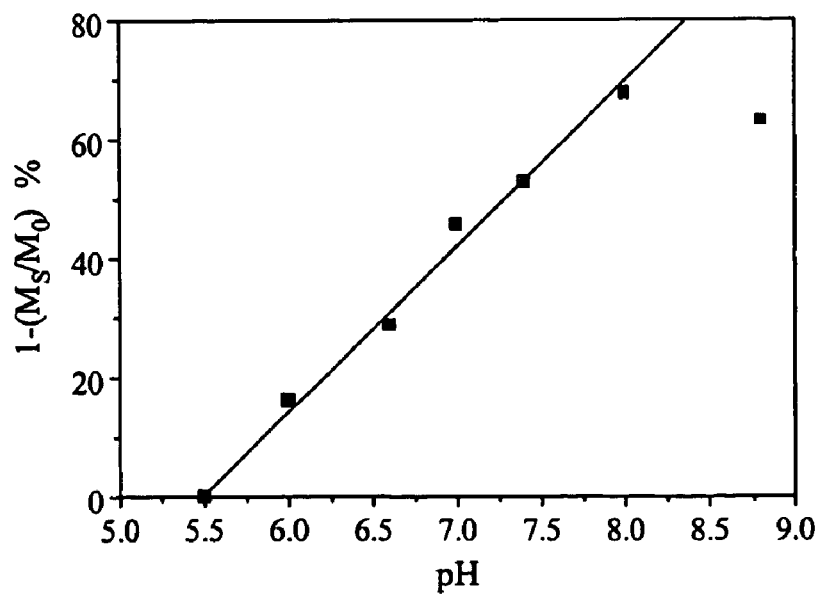
Figure 6 Bis

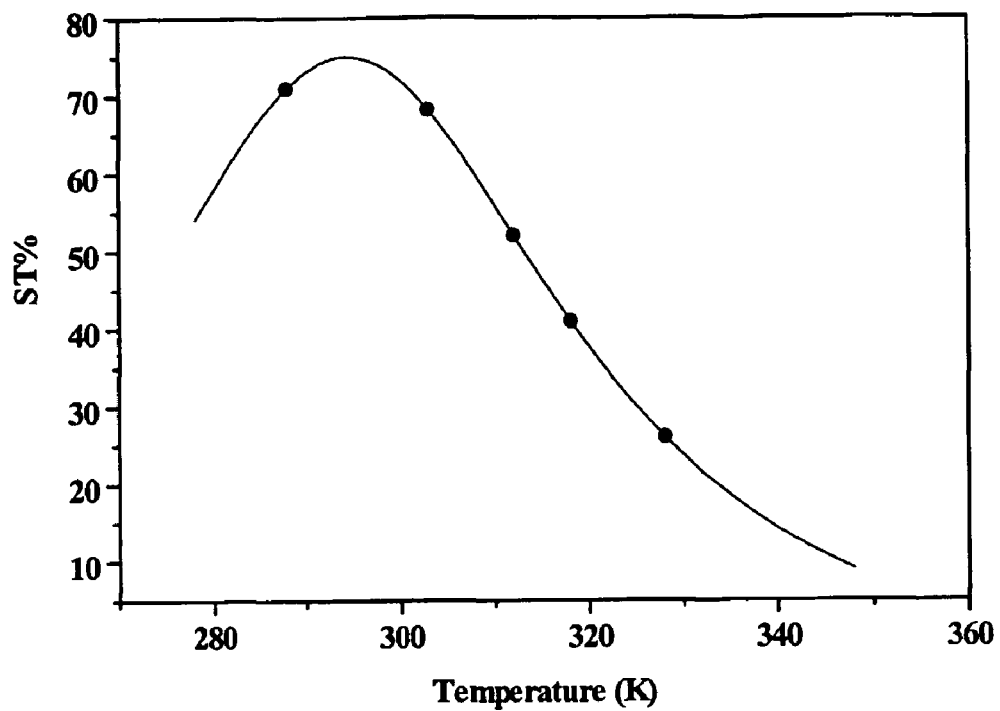
Figure 13
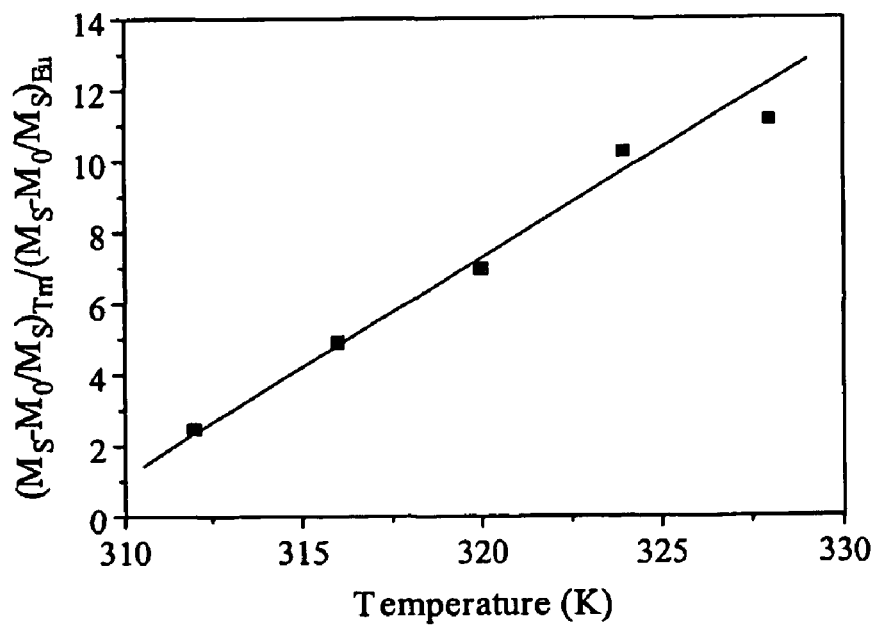
Figure 13 Bis

RESPONSIVE PARAMAGNETIC MRI CONTRAST AGENTS This application is the national stage filing of corresponding international application number PCT/EP03/00796, filed Jan. 27, 2003, which claims priority to and the benefit of European Application No. 02001178.9, filed Jan. 29, 2002, all of which are hereby incorporated by reference.

This invention refers to a method based on CEST procedure for the in vivo, ex vivo, or in vitro determination of physical or chemical parameters of diagnostic interest comprising the use of at least one CEST responsive paramagnetic contrast agent.

BACKGROUND OF THE INVENTION

It is now well established that the potential of Magnetic Resonance Imaging (MRI) procedures can be further enhanced when this diagnostic modality is applied in conjunction with the administration of contrast agents (CAs), i.e. chemicals able to promote marked changes in the relaxation rates of the tissue protons. According to the major effects they produce on images, CAs are classified as positive or negative agents. The positive CAs are represented by paramagnetic complexes, mostly containing Gd(III) or Mn(II) ions, which affect the relaxation rates of the bulk water through the exchange of the water molecules in their coordination spheres (Caravan P, et al. Chem Rev 1999, 99:2293-2352; the Chemistry of Contrast Agents in Medical Magnetic Resonance Imaging. Chichester, UK: John Wiley & Sons; 2001. p 45-120). Their effect is similar on $T_1$ and $T_2$ but, being $T_1$ usually significantly longer than $T_2$ in most biological tissues, their effect is more often exploited in $T_1$-weighted images, thus resulting in brighter spots in the images.

On the contrary, negative CAs are used to shorten $T_2$, leading to an improved contrast by reducing the water signal in $T_2$-weighted images.

Furthermore, it was early reported that chemicals containing mobile protons may act as $T_2$-agents through the reduction of the water proton relaxation time via exchange processes (Aime S et al., Invest Radiol 1988; 23(Suppl 1):S267-S2706).

A different way to efficiently reduce water signal occurs when a proper radiofrequency pulse (rf) is applied at the resonance frequency of an exchangeable proton saturating it. This results in a net decrease of the bulk water signal intensity owing to a saturation transfer effect.

This alternative MRI contrast-enhancing technique is named Chemical Exchange Dependent Saturation Transfer (CEDST or, more commonly, CEST) (Balaban R S.: Young I R, editor. Methods in Biomedical Magnetic Resonance Imaging and Spectroscopy. Chichester, UK: John Wiley & Sons; 2000. Vol. 1. p 661-6667).

Suitable contrast agents for this technique include at least one chemically exchangeable proton.

The efficacy of most prior art contrast agents, either the conventional $T_1$ and $T_2$-reducing MRI contrast agents or the CEST agents, is related to the different cellular uptake of the administered complex compound or to the different distribution thereof through the extracellular spaces of the targeted organ or tissue. No contrast is detectable if the uptake between the target and the surrounding tissue is similar.

Moreover, the prior art contrast agents are expressly addressed to the production of images of the targeted tissue or organ and, generally, are unable to act as reporter of specific physical or chemical parameters of the examined tissue which could represent a quantitative assessment of a physio/pathological state.

Otherwise, WO 00/66180 discloses a method for enhancing the contrast of MRI images which comprise the administration of a CEST MRI contrast agent including at least one chemical group endowed with appropriate proton exchange and chemical shift properties to function effectively for performing CEST MRI analyses in vivo as well as for the determination of physical or chemical parameters such as pH and temperature both in vivo and in vitro. A ratiometric method for the pH measurement which is independent on the contrast agent concentration is also disclosed.

All the agents disclosed by Balaban and co-workers as useful to practice the claimed method are diamagnetic organic molecules having OH or NH exchangeable protons.

In general, the mobile protons of a contrast agent for a CEST application must possess a fast exchange rate ($k_{ex}$) with water protons, but slower than the coalescence condition, wherein this condition is suitably reached when $k_{ex}\Delta v \sim 1/2\pi$, where $\Delta v$ is the chemical shift separation in Hz between the two exchanging pools. In this context, larger $\Delta v$ values enable the exploitation of higher $k_{ex}$ values, thus resulting in an enhanced CEST effect.

The diamagnetic systems claimed by Balaban are advantageously endowed with adequately short relaxation rates, but the chemical shifts separation from their NH or OH exchangeable protons signals and the bulk water signal is only within 1-5 ppm. So, the saturation of these mobile protons, avoiding the saturation of the bulk water or protein bound water, could actually present a considerable difficulty. Beside the small $\Delta v$ values, a further limit of such diamagnetic agents is represented by the high concentration thereof which is usually required to generate a sufficiently large CEST effect, resulting in a high probability of toxic or physiological effect in vivo.

WO 02/43775 discloses paramagnetic metal ion-based macrocyclic CEST contrast agents which comprises a tetraazacyclododecane ligand wherein pendent arms includes amide groups, a paramagnetic metal ion coordinated to the ligand and a water molecule associated with it. Said agents are reported to be useful for producing image contrast based on a magnetization transfer mechanism.

The specification cites the effect of the pH on the residence lifetime at 298 K, $\tau_M^{298}$, ($\tau_M=1/k_{ex}$) for protons associated with the amides in the pendent arms and the pH dependence of the Magnetization Transfer effect obtained while saturating two magnetically different exchangeable protons associated to the same amide group of one of claimed compounds (FIG. 25 and experiment 13, respectively). The specification, however, fails to teach or even suggest the applicability of the pH effect on the magnetization transfer to the whole class of claimed agents. Moreover, either the specification or the experiment 13 fail to teach or to suggest the possible use of the claimed compounds in a method of general applicability for the determination of a physical or chemical parameter of diagnostic interest in a human or animal body organ, fluid or tissue; even less in a method wherein said determination is obtained independently on the local contrast agent concentration. At the same time, WO 02/43775 specification fails to teach how said determination may be carried out.

SUMMARY OF THE INVENTION

The present invention relates to a method based on the CEST procedure for the in vivo, in vitro or ex vivo determination of a physical or chemical parameter of diagnostic interest which includes the administration of a responsive paramagnetic CEST contrast agent.

In particular, it is an object of the present invention a method for the determination, by use of the Magnetic Resonance Imaging technique, of a physical or chemical parameter of diagnostic interest in a human or animal body organ, fluid or tissue wherein:

a responsive paramagnetic CEST contrast agent is employed comprising at least one exchangeable proton whose saturation capability is correlated to the physical or chemical parameter of interest, and a CEST MR image which is responsive for said parameter in the organ or tissue under examination is registered.

The paramagnetic contrast agent for use in the method of the invention is a responsive agent, i.e. an agent which combines the characterising features of a CEST agent with the fact that the saturation transfer effect that it enables is sensitive to the physical or chemical parameter of diagnostic interest. Accordingly, the contrast agent for use in the method of the invention is a paramagnetic compound which comprises at least one mobile proton in chemical exchange with the water medium protons and which is able, when a proper radiofrequency irradiating field is applied at the resonance frequency of the said exchangeable proton, to generate a saturation transfer (ST) effect between said mobile proton and the water medium protons that only correlates to the physico-chemical parameter of diagnostic interest.

In a preferred method according to the invention, a CEST paramagnetic contrast agent is administered which is endowed with at least two magnetically different mobile protons or proton pools allowing the registration of CEST MR image responsive for the physico-chemical parameter of diagnostic interest and independent on the administered contrast agent concentration.

The responsive paramagnetic CEST contrast agents for use in the method of the invention overcome the limits affecting the prior-art diamagnetic compounds of WO 00/66180. The molecular structure of the paramagnetic responsive agents according to the present invention, in fact, can advantageously be selected in order to pursue optimal values for the chemical shifts and exchange rates of the mobile protons with water protons. Further, the structures of the diamagnetic agents of WO 00/66180 include a relatively small number of mobile protons which can not be easily increased. Conversely, the number of labile protons on the responsive CEST agents according to the invention can advantageously be increased with consequent reduction of the amount of administered agent.

When compared to WO 02/43775, the present invention provides a general method for the determination of a physical or chemical parameter of diagnostic interest in a human or animal body organ, fluid or tissue. The method is based on the use of a paramagnetic CEST contrast agent which is responsive for said parameter. According to this method, a determination may be performed which is independent on the local concentration of the administered agent.

The responsive paramagnetic agent for use in the method of the invention preferably includes at least one chelated complex of a paramagnetic metal ion. The paramagnetic metal ion is any transition or lanthanide (III) metal ion which has an electronic relaxation time suitably short to significantly affect the chemical shift value of the mobile protons to be irradiated. Preferred paramagnetic metal ions are selected in the group consisting of: iron (II) (high spin), iron (III), cobalt (II), copper (II), nickel (II), praseodymium (III), neodymium (III), dysprosium (III), erbium (III), terbium (III), holmium (III), thulium (III), ytterbium (III), and europium (III).

Lanthanide (III), also referred to as Ln(III), metal ions are particularly preferred.

The chelating ligand of the paramagnetic complex for the use in the method of the invention can be any organic ligand endowed with at least one mobile proton bound to a nitrogen, oxygen, sulphur or phosphorous atom. Preferably, the mobile proton belongs to an amide group coordinated to the metal ion.

A further suitable source of mobile protons according to the invention is represented by the water molecule(s) coordinated to the paramagnetic centre of the chelated complex. In this particular case the relaxation time of the bulk water protons is influenced by the exchange thereof with the inner-sphere coordinated water protons.

Responsive agents for use in the method of the invention includes the chelates of the macrocyclic tetra-amide derivatives of the 1,4,7,10-tetraazacyclododecane-1,4,7,10-tetraacetic acid (DOTA), the tris-amide derivatives of the 1,4,7,10-tetraazacyclododecane-1,4,7-triacetic acid (DO3A) and the derivatives of the hexa-aza-macrobicycle sarcophagine (3,6,10,13,16,19-hexaazabicyclo[6.6.6]eicosane) with the preferred metal ions indicated above.

Preferred paramagnetic contrast agents which include a chelating ligand of formula (I) are:

where:

| | |
|---|---|
| R = R' = R'' = R''' = —CH$_2$—CONH—CH$_2$COOH | Ligand A |
| R = R' = R'' = R''' = —CH$_2$—CONHNH$_2$ | Ligand B |
| R = R' = R'' = —CH$_2$—CONH$_2$ 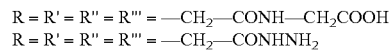 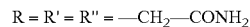 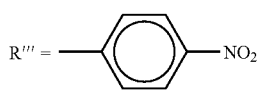 R''' = —⟨C$_6$H$_4$⟩—NO$_2$ | Ligand C |
| R = R' = R'' = —CH$_2$—CONH$_2$ 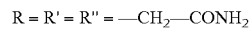 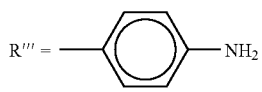 R''' = —⟨C$_6$H$_4$⟩—NH$_2$ | Ligand D |

-continued

| | | |
|---|---|---|
| R = R' = R" = —CH$_2$—CONH$_2$ | R''' = —⟨phenyl⟩—CH$_2$COOH | Ligand E |
| R = R' = R" = —CH$_2$—CONH—CH$_2$—COOBu | R''' = —⟨phenyl⟩—NO$_2$ | Ligand F |
| R = R' = R" = —CH$_2$—CONH$_2$ | R''' = —CH$_2$—⟨phenyl⟩—OCH$_3$ | Ligand G |
| R = R' = R" = —CH$_2$—CONH$_2$ | R''' = —CH$_2$—NHSO$_2$—⟨phenyl⟩—COOH | Ligand H |
| R = R' = R" = —CH$_2$—CONH—CH$_2$COOH | R''' = —CH$_2$—CONH(CH$_2$)$_2$NH—C(=S)—NH—⟨phenyl⟩—NH—⟨phenyl⟩—SO$_3^-$ | Ligand L |

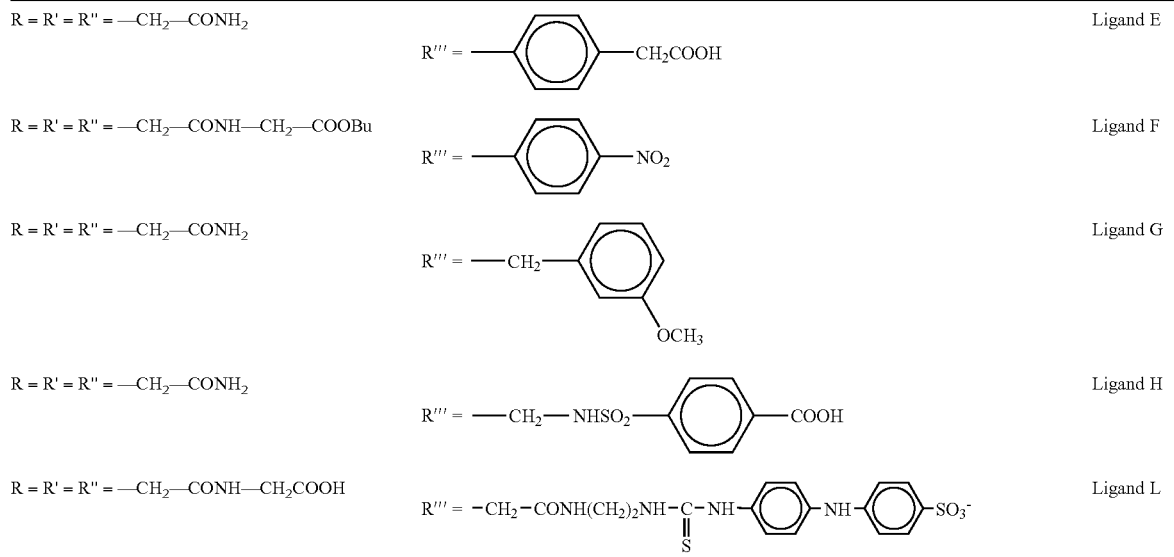

which is chelated to a Ln(III) metal ion, and which further preferably includes a water molecule coordinated to the paramagnetic metal centre thereof.

Another preferred class of compounds includes paramagnetic complexes having a chelating ligand of formula (II):

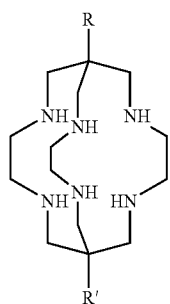

(II)

where:

*R=R'=—NO$_2$        Ligand M

The 1,4,7,10-tetraazaciclododecane-1,4,7,10-acetic acid tetraazide derivative of formula

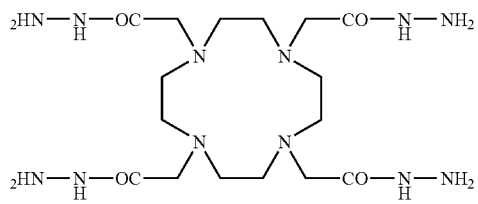

herein referred to as ligand B or DOTAM-hydrazide, as well as the chelated thereof with the transition or the lanthanide (III) metal ions are new and are a further object of the present invention.

The 1,4,7,10-tetraazaciclododecane-1,4,7,10-acetic acid tetraglycineamide chelating ligand of formula:

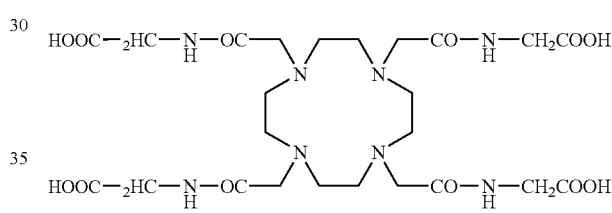

is herein referred to as ligand A or DOTAM-Gly.

The CEST effect arising from the irradiation of the amide N—H protons of the Ln(III) complex compounds according to the invention has been tested on the basis of a series of CEST experiments in which the ST effect is measured as a function of the irradiation time (irradiation power of 25 μT, where T means Tesla). In particular five Ln-DOTAM-Gly chelates in which Ln=Dy, Ho, Er, Tm, Yb were tested. The experimentation results included in FIG. 3 show that the most efficient saturation transfer is observed for the Yb(III) complex (30 mM) at pH 8.1 wherein the observed saturation effect of ca. 70% after 2 s of irradiation appears indicative of a very efficient saturation transfer. To reach similar results with diamagnetic molecules, such as aminoacids, a much higher concentration (125 mM) is requested. Furthermore, similar results are obtained only at pH 5, that is to say at pH values that are far from the physiological range (Ward K M et al. J Magn Res 2000; 143: 79-87).

As far as other Ln(III)-DOTAM-Gly complexes are concerned, the data reported in FIG. 3 indicate a clear trend in the saturation transfer effect along the lanthanide series on passing from the Dy(III) chelate, for which the CEST effect is minimal, to the Yb(III) complex.

The overall visualization of the ST effects is represented by a CEST spectrum, an example of which is reported in FIG. 4 for a 30 mM solution of Yb-DOTAM-Gly at pH 8.1. The spectrum reports the intensity of the water signal, normalized to the higher value, as a function of the irradiation offset.

Obviously, the effect is maximum at the resonance frequency of water (0 ppm), but it is immediately evident that when the irradiation frequency is set to ca. −16 ppm from water, a significant water saturation is observed and the residual signal is slightly less than 20%. However, since this effect may be partly accompanied by the direct saturation of the water signal, the "true" CEST effect is quantitatively assessed by considering also the off-resonance saturation. This means that the value of the $M_S/M_0$ ratio measured in the experiment reported in FIG. 3 is the ratio of the two values indicated by the arrows in the FIG. 4.

For the Eu-DOTAM-Gly chelate the chemical shift separation between the amide protons and the bulk water is smaller (4.2 ppm) than the other Ln(III) ions tested (see FIG. 2). The irradiation of the amide protons with the same square pulse used for the other Ln-DOTAM-Gly complexes does not allow the detection of a saturation transfer effect owing to a remarkable direct saturation effect on the bulk water. For this reason, it is convenient to use a selective shaped saturation pulse. The ST effect measured by using a train of 270° e-burp1 pulses of 20 ms each (total irradiation time 4 s, irradiation power 1.2 µT) was of 23% (pH 7.7, 30 mM, 312° K, 7.05 T).

It is now noteworthy to consider that in this chelate it is also possible to detect a saturation transfer effect by irradiating the water protons coordinated to the Eu(III) ion which resonate at ca. 50 ppm downfield from bulk water at 312° K. Since this signal is extremely broad, it is again convenient to use a selective shape pulse in order to excite all the spins simultaneously. On this basis, a remarkable ST effect of ca. 85% has been measured (train of 90° e-burp1 pulses of 1 ms each, total irradiation time 4 s, irradiation power 15.7 µT, pH 7.7, 30 mM, 312° K, 7.05 T).

The ST effect shown by the lanthanide chelated complex according to the invention is further markedly sensitive to physical or chemical parameters of diagnostic interest wherein this allows their advantageous use in the method of the invention for the determination of said parameters either in vivo or in vitro.

A list of parameters of interest includes any physical or chemical parameter of diagnostic interest which is able to influence at least one factor which regulates the saturation transfer from the contrast agent and the surrounding water.

In particular said parameters include: temperature, pH, metabolite concentration, $O_2$ or $CO_2$ partial pressure, enzymatic activity, in a human or animal body organ or tissue.

According to the method of the invention the amount of saturation transfer is related to the physical or chemical parameters of diagnostic interest according to the following equation:

$$\left(1 - \frac{M_s}{M_0}\right) = \left[\frac{k_{ex}n[C]}{2R_{1irr}[H_2O] + k_{ex}n[C]}\left(1 - \exp\left[-\left(R_{1irr} + \frac{k_{ex}n[C]}{2[H_2O]}\right)t\right]\right)\right] \quad [1]$$

According to this equation, the saturation transfer effect observed is conveniently quantified as $(1-M_S/M_0)$ wherein Ms refers to the intensity of the water signal upon irradiation at the frequency corresponding to the mobile protons resonance ($v^{on}$) and $M_0$ indicates the water signal intensity measured upon irradiation at the frequency $v^{off}$ where $v^{off}=-v^{on}$ and $v^{water}=0$.

The irradiation at $v^{off}$ allows the evaluation of the direct saturation effects on the water signal.

As indicated by equation 1, the ST effect is dependent on:

the irradiation time, t;
the pseudo first order kinetic constant rate of the irradiated protons $k_{ex}$;
the number of irradiated mobile protons n;
the longitudinal relaxation rate of the bulk water upon irradiation of the mobile protons, $R_{1irr}$;
the molar concentration of the paramagnetic agent, [C] and of the bulk water protons, [$H_2O$] (111.2 M in pure water).

One can safely assume that all the paramagnetic chelates preferred for the use in the method of the invention possess an exchangeable water molecule coordinated to the metal centre. For this reason, though $R_{1irr}$ is conceptually different from $R_1$, it is likely that $R_{1irr}$ is higher for paramagnetic systems than diamagnetic agent and, furthermore, it depends on both the concentration of the metal complex and the $k_{ex}$ value.

Equation 1 indicates that the ST efficiency depends upon the concentration of the exchanging protons and therefore on the concentration of the contrast agent (n[C]). This finding makes the measurement of the diagnostic parameter of interest dependent on the contrast agent concentration. So, while no problems occur when the determination of said parameters is performed in vitro, where the concentration may be determined, an accurate in vivo determination thereof without knowing the local concentration of the administered agent is not possible.

The relationship between the concentration of the paramagnetic agent and the ST effect is not linear, unlike what is commonly observed for the relaxation enhancing ability of the conventional Gd(III)-based contrast agents. In fact, the steady-state value of the ST effect is determined by:

$$\left(1 - \frac{M_s}{M_0}\right) = \frac{k_{ex}n[C]}{2R_{1irr}[H_2O] + k_{ex}n[C]} \quad [2]$$

where it is evident that the dependence of the concentration of the contrast agent is less marked than in the conventional MRI contrast agents, even by taking into account the concentration dependence of $R_{irr}$.

So, in spite of the limited role played by the concentration on the efficacy of a CEST contrast agent, the precise knowledge of the local concentration of the agent is still a necessary requisite for an accurate determination in vivo of the parameter to be monitored.

This problem may be solved by considering two pools of magnetically different labile protons whose ST effect shows a different dependence from the physico-chemical parameter of interest according to the preferred method of the invention. To reach this aim, two strategies are indeed possible:
i) the use of a paramagnetic contrast agent comprising a single CEST molecule endowed with both the two magnetically non equivalent mobile protons pools, or
ii) the use of a paramagnetic contrast agent comprising two different CEST units endowed with at least one set of mobile protons each. In the latter case the two molecules must have the same biodistribution pattern.

In a first preferred method for the determination of physical or chemical parameters of diagnostic interest independently on the local contrast agent concentration, a single paramagnetic compound having at least two magnetically non equivalent pools of mobile protons in exchange with the bulk water protons is used.

According to this method, the selective irradiation is performed on the two different pools of mobile protons. A ratiometric method is then exploited in order to remove the dependence of the ST effect from the absolute concentration of the administered contrast agent and to allow the determination of the physico-chemical parameter of interest both in vitro (ex vivo) and in vivo independently from the local concentration of the agent.

Preferably, the compound is a paramagnetic complex or a physiologically acceptable salt thereof. The metal ion is preferably selected among paramagnetic transition or Ln(III) metal ions on the basis of the ability to induce the ST effect through the involvement of two magnetically different sets of mobile protons belonging to the paramagnetic complex molecule. The chelating ligand may consist of any organic monomeric ligand endowed with at least two pools or, if one pool is represented by the water protons coordinated to the metal centre of the paramagnetic complex, at least one pool of mobile protons bound to a nitrogen, oxygen, sulphur, phosphorous atom. Preferably, the mobile protons pools belong the first to an amide group of the chelating ligand and the second to the metal coordinated water protons. More preferably, the mobile protons pools belong the first to the coordinating amide groups and the second to the metal bound water protons of the Eu(III) complexes of the chelating ligands A, C, D, E, F, G, H, L.

A different contrast agent for use in this preferred method includes a paramagnetic complex or a physiologically acceptable salt thereof wherein the chelating ligand consist of a dimeric ligand which includes two equal or different chelating units each of them is endowed with at least one pool of mobile protons and the two metal ions are suitably selected among the transition or Ln(III) metal ions on the basis of their ability to induce a different ST effect through the involvement of the two sets of mobile protons pools. The mobile protons pools are preferably represented: the first, by the water protons coordinated to the metal ion of the first moiety, and the second by mobile protons bound to a nitrogen, oxygen, sulphur, phosphorous atoms of the second moiety, or both of them may optionally be represented by the water protons coordinated to two different Ln (III) metal ions or by mobile protons bound to a nitrogen, oxygen, sulphur or phosphorous atoms.

More preferably, the mobile protons pools belong, the first to the water protons coordinated to the Eu(III) metal ion and the second to the amide groups coordinated to the Yb(III) of the dimeric complex compound [Eu—Yb(bisDOTAMGLy)] of formula According to this method, the selective irradiation is performed of two different pools of mobile protons, which are provided by the two paramagnetic agents. A ratiometric method is again exploited which removes the dependence of the saturation transfer effect from the absolute concentration of the administered contrast agents. This method allows the determination of said physical or chemical parameter both in vitro (ex vivo) and in vivo independently from the local concentration of the agent but according to the known concentration ratio between the two agents.

Preferably, the two paramagnetic compounds are paramagnetic chelate complexes or a physiologically acceptable salt thereof in which the two chelated paramagnetic ions are different. Said two metal ions are preferably selected among paramagnetic Ln(III) ions on the basis of their ability to promote the saturation transfer effect through the involvement of two magnetically different exchanging proton pools. The two chelating ligands may consist of any organic ligand endowed with at least one mobile proton bound to a nitrogen, oxygen, sulphur, phosphorous atom and may be equal or different but suitably selected in order to grant the same biodistribution pattern for the two metal complexes. Preferably the mobile protons belong to an amide group and, more preferably, to the coordinating amide groups of a chelating ligand selected among: 1,4,7,10-tetraazaciclododecane-1,4,7,10-tetraacetic acid tetraglycineamide (ligand A), 10-[(3-methoxyphenyl)methyl]-1,4,7,10-tetraazaciclododecane-1,4,7-tris-[(aminocarbonyl)methyl] (ligand G) or to the metal coordinated water protons in the tetrahydrazide derivative (ligand B).

Even more preferred is the use in this method of a contrast agent which comprises Yb(III)-DOTAM-Gly together with Eu(III)-DOTAM-Gly or a physiologically acceptable salt thereof. The first complex has been chosen for the availability of chemically exchanging amide protons ($\Delta\delta$=16 ppm at 312° K) and the second one for the protons belonging to metal coordinated water molecule ($\Delta\delta$ of ca. 50 ppm at 312° K).

Equally preferred is the use of Tm(III)-DOTAM-Gly (irradiation of amide protons) together with Eu(III)-DOTAM-Gly or a physiologically acceptable salt thereof.

Having the same electric charge, hydrophilic/lipophilic balance and analogous structure, the two metal complexes of both the couples are reasonably expected to show the same biodistribution pattern.

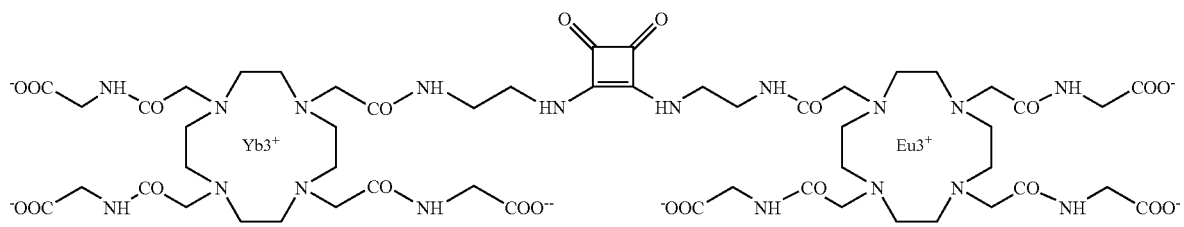

The (bisDOTAMGLy) dimeric chelating ligand as well as chelated complexes thereof with two transition or Ln(III) paramagnetic metal ions are new and constitute a further object of the present invention.

According to the second strategy, in another preferred method for the determination of physical or chemical parameters of diagnostic interest by use of CEST MRI imaging, two paramagnetic complex compounds are used. In this case, the two CEST agents must have the same biodistribution pattern.

In the most preferred method according to the invention for the determination of physical or chemical parameters of diagnostic interest independently on the local contrast agent concentration a responsive paramagnetic CEST contrast agent is administered endowed with at least two different exchangeable proton or protons pools of which the first is only responsive for the physical or chemical parameter of diagnostic interest and the second shows a CEST effect which only depends on the local agent concentration.

According to this method, the selective irradiation is performed of the two different pools of mobile protons and the determination of the physical or chemical parameter of interest both in vitro (ex vivo) and in vivo is obtained which is independent on the local contrast agent concentration.

A further object of the invention is the use of a CEST contrast agent comprising a paramagnetic chelate complex endowed with at least one mobile proton in chemical exchange with the water medium protons and able, when a proper radiofrequency rf irradiating field is applied at the resonance frequency of said exchangeable proton, to generate a saturation transfer effect between said mobile proton and the water protons which is sensitive to a physical or chemical parameter of diagnostic interest for the preparation of a pharmaceutical composition for the determination of said parameter in a human or animal body organ, fluid or tissue by use of CEST MR Imaging.

Preferably said paramagnetic compound(s) include a chelating ligand of formula (I)

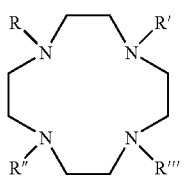

(I)

where:

Another preferred paramagnetic compound(s) include a chelating ligand of formula (II)

(II)

where:

*R=R'=—NO$_2$     Ligand M

Even preferably said paramagnetic compound is the [Eu—Yb(bisDOTAMGLy)] chelated complex.

In an even further aspect the invention relates to the use of two paramagnetic chelated complex which must exhibit the same biodistribution pattern, each of them comprising at least one mobile proton in chemical exchange with the water medium protons for the preparation of a pharmaceutical composition for the determination of a physical or chemical parameter of diagnostic interest in a human or animal body

| | | |
|---|---|---|
| R = R' = R'' = R''' = —CH$_2$—CONH—CH$_2$COOH | | Ligand A |
| R = R' = R'' = R''' = —CH$_2$—CONHNH$_2$ | | Ligand B |
| R = R' = R'' = —CH$_2$—CONH$_2$ | R''' = 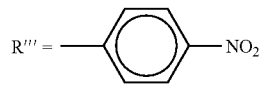 | Ligand C |
| R = R' = R'' = —CH$_2$—CONH$_2$ | R''' = 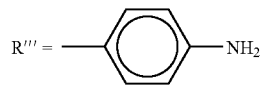 | Ligand D |
| R = R' = R'' = —CH$_2$—CONH$_2$ | R''' = 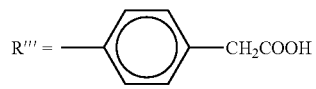 | Ligand E |
| R = R' = R'' = —CH$_2$—CONH—CH$_2$—COOBu | R''' = 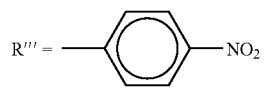 | Ligand F |
| R = R' = R'' = —CH$_2$—CONH$_2$ | R''' = 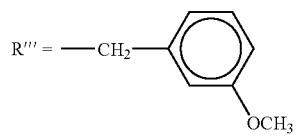 | Ligand G |
| R = R' = R'' = —CH$_2$—CONH$_2$ | R''' = 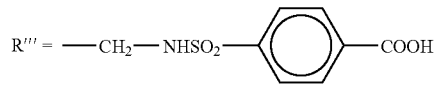 | Ligand H |
| R = R' = R'' = —CH$_2$—CONH—CH$_2$COOH | R''' = 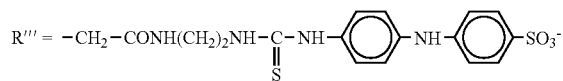 | Ligand L | which is chelated to a Ln(III) metal ion.

organ, fluid or tissue independently on the local contrast agent concentration, by use of CEST MR Imaging. Preferred is the use for this scope of Yb(III)-DOTAM-Gly together with Eu(III)-DOTAM-Gly or a physiologically acceptable salt thereof or, optionally, Tm(III)-DOTAM-Gly together with Eu(III)-DOTAM-Gly.

In an even further aspect the invention relates to a pharmaceutical composition which includes, together with a physiologically tolerable carrier, a CEST contrast agent comprising a paramagnetic chelate complex, or a physiologically acceptable salt thereof, which comprises at least one, and preferably at least two, mobile protons or proton pools in chemical exchange with the water medium protons able, when a proper radiofrequency rf irradiating field is applied at the resonance frequency of the said exchangeable protons, to generate a saturation transfer effect between said mobile proton and the water protons which is only sensitive to the physical or chemical parameter of diagnostic interest.

This pharmaceutical composition preferably includes, together with a physiologically tolerable carrier, a paramagnetic chelated complex selected among: Eu(III)-DOTAM-Gly, Eu(III)-DOTAM-hydrazide, Co(II)(high spin) chelate complex of the ligands G and M, the Ln(III) chelate complexes of the chelating ligands C, G, H and L, [Eu—Yb (bisDOTAMGLy)] or a physiologically acceptable salt thereof.

Also preferably, the pharmaceutical composition includes, together with a physiologically tolerable carrier, two paramagnetic chelated complexes or a physiologically acceptable salt thereof wherein the two paramagnetic metal ions are different and the chelating ligands, which may consist of any organic ligand endowed with at least one mobile proton bound to a nitrogen, oxygen, sulphur, phosphorous atom, are suitably selected in order to grant the same biodistribution pattern for the two metal complexes. More preferably the chelating ligand are both the same.

The two paramagnetic complexes are preferably comprised in equal molar amount or in a known molar ratio which is selected according to the chelated metal ions. Said ratio may range from 1 to 30, preferably it ranges from 1 to 10, more preferably from 1 to 5 and most preferably from 1 to 2, wherein the minimum molar concentration requested of the paramagnetic compound included in lower amount is at least 0.05 mM while the global concentration of the included paramagnetic CEST contrast agent ranges between 0.001 and 1.0 M.

Most preferably, this pharmaceutical composition comprises Yb(III) DOTAM-Gly together with Eu(III) DOTAM-Gly or Tm-DOTAM-Gly together with Eu-DOTAM-Gly, or a physiologically acceptable salt thereof, together with a physiologically acceptable carrier.

The pharmaceutical preparations according to the invention can be suitably injected intravasally (for instance intravenously, intraarterially, intraventricularly, and so on) or used by way of intrathecal, intraperitoneal, intralymphatic, intracavital, oral or enteral administration.

The injectable pharmaceutical formulations are typically prepared by dissolving the active ingredient(s) and the pharmaceutically acceptable excipients in water of suitable purity from the pharmacological point of view. The resulting formulation is suitably sterilised and can be use as such or it can alternatively be lyophilised and reconstructed before the use.

These formulations can be administered in concentrations depending on the diagnostic requirements, at a dose ranging from 0.01 to 0.5 mmol/kg body weight.

In order to test the validity of a preferred method according to the invention the CEST spectra of a solution containing 16 mM of Eu-DOTAM-Gly and 20 mM of Yb-DOTAM-Gly at pH 8.1 (7.05 T, 312° K, irradiation power 25 µT, irradiation time 4 s) were registered and the results are included in FIG. 8. Interestingly, the detection of a "peak" (very broad) centred at about 50 ppm (downfield the water signal) is a clear indication of the saturation transfer occurring when the coordinated water protons of Eu-DOTAM-Gly are irradiated.

The ratiometric method on which is based the preferred method according to the invention is derived from a re-arrangement of equation 1 and it is expressed by the following equation:

$$\frac{\left(\frac{M_0 - M_s}{M_s}\right)^A}{\left(\frac{M_0 - M_s}{M_s}\right)^B} = \frac{K^{conc} k_{ex}^A n^A R_{1irr}^B}{k_{ex}^B n^B R_{1irr}^A} \quad [3]$$

where the superscripts A and B identify the paramagnetic complex compounds whose exchanging pools magnetic parameters are referred to. In the above experimentation, for example, A=Yb-DOTAM-Gly and B=Eu-DOTAM-Gly and $K^{conc}$ which represents the [A]/[B] ratio is 1.25. The presence of two $R_{1irr}$ values, one for each pool of labile proton irradiated, is due to the fact that, in principle, $R_{1irr}$ depends on the exchange rate between the bulk water and the irradiated mobile protons which is different for the two proton pools.

The same equation holds also if one single compound with two pools of mobile protons is considered, but, in this case, $K^{conc}$ is obviously equal to 1.

pH Responsive CEST Agents

Generally speaking, a good candidate as pH responsive CEST agent according to the method of the invention may be any paramagnetic complex compound which includes a Ln(III) metal ion or a transition metal and a chelating ligand which comprises at least one mobile proton whose chemical exchange with the water protons undergoes a basic or acid catalysis.

Moreover, any paramagnetic complex whose structure changes according to the pH in such a way to induce a chemical shift modification of the mobile proton(s) thereof can equally be used as pH responsive CEST agent according to the method of the invention.

Suitable pH responsive CEST agents further include all the paramagnetic complex compounds wherein the number of water molecules coordinated to the paramagnetic metal centre changes depending on the pH and a change of the relaxation rate of the bulk water protons occurs. A pH responsive agent of this kind is represented, for example, by a Ln(III) chelated complex of the chelating Ligand H of formula

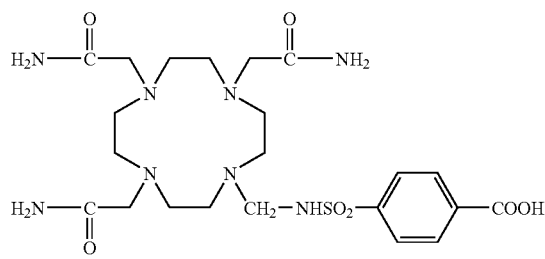

When the sulphonamide group is in the protonated form, the Ln(III) ion is nona-coordinated and two mobile water molecules are bound to the metal centre. On the contrary, when the sulphonamide group is deprotonated it becomes able to coordinate the metal ion which result to be octa-coordinated (no water molecules coordinated to it). The chemical shift of the 6 exchangeable amide protons on the three pendent arms depends on the molar ratio between the protonated and the deprotonated form of the complex, that is to say with the pH of the solution. In this way the saturation transfer effect upon irradiation of the amide protons of the complex (in the protonated or in the deprotonated form) is sensitive to the pH of the surrounding medium.

A further example of pH responsive paramagnetic CEST agent is represented by the Eu-DOTAM-hydrazide (ligand B) chelated complex. In this compound a proton dissociation, occurring at pH above 6.5, causes a significant acceleration of the exchange rate of the water molecule bound to Eu(III) ion on passing from the condition of slow exchange ($k_{ex}\Delta v < 1/2\pi$) at pH<6.5 to the coalescence ($k_{ex}\Delta v > 1/2\pi$) between the two signals. Indeed, the ST observed upon irradiation at the resonance frequency of the water protons bound to the Eu(III) ion ($\Delta v$ of 15000 Hz) decreases at pH values higher than 6.5 (FIG. 5).

As the pH dependence of the ST effect promoted by the mobile protons of amide groups thereon, the Ln(III) DOTAM-Gly and the Ln(III)-Ligand G complexes represent an example of suitable class of pH responsive CEST agents.

The pH dependence of the ST effect has been assessed for the Yb-Ligand G complex compound (20 mM, 312° K, irradiation power 25 µT, irradiation time 4 s) and the results are showed in FIG. 6. The ST effect is markedly pH-dependent, being maximum at pH 7.2 and almost negligible at pH values lower than 5.5.

The pH dependence of the ST effect has been also assessed for the Yb-DOTAM-Gly derivative (30 mM, 312° K, irradiation power 25 µT, irradiation time 4 s) and the results are showed in FIG. 6 Bis. The ST effect is markedly pH-dependent, being maximum at pH 8.1 and almost negligible at pH lower than 6. The pH dependence is linear (regression coefficient=0.996) in the pH range 5.5-8.1, whereas at higher pH values the saturation transfer becomes less efficient likely because of the too extensive exchange broadening of the N—H resonances. This behaviour supports the hypothesis that the pH dependence of the ST effect mainly arises from the base-catalysed proton exchange of the amide N—H protons of the Yb(III) complex. Interestingly, similar results were obtained upon 2 s of irradiation. These results are very promising for an in vivo application of this chelate, since the ST effect is markedly pH sensitive and, moreover, it is properly tuned at the physio-pathological pH interval.

A standard proton density (PDW) $^1$H water MR image of a phantom containing a 30 mM solution of the agent at different pH values was further recorded at 7.05 T and 298° K on a Bruker Pharmascan imager (FIG. 7). Interestingly, even at pH 5.4, where the directly measured CEST effect is quite low (12%), the corresponding contrast in the image difference is not negligible at all.

According to the preferred method of the invention, the pH dependence of the CEST effect has been tested by using a mixture of two Ln(III)-DOTAM-Gly chelates differing in the lanthanide ion. Thus, Yb-DOTAM-Gly and Eu-DOTAM-Gly complexes were chosen in order to exploit the CEST effects associated with the exchange of the amide N—H protons and the metal coordinated water protons, respectively. In FIG. 8 the CEST spectrum obtained from a solution containing 16 mM of Eu-DOTAM-Gly and 20 mM of YbDOTAM-Gly at pH 8.1 ($B_0$=7.05 T, 312° K, irradiation power 25 µT, irradiation time 4 s) is shown. Besides the peak due to the direct saturation of the bulk water, the CEST spectrum is characterized by two additional peaks: one, relatively narrow, is upfield shifted of ca. 16 ppm and the other, very broad, is downfield shifted at ca. 50 ppm from the chemical shift of the bulk water. Clearly, the first peak corresponds to the four amide N—H protons of the Yb(III) complex, whereas the second peak refers to the protons of the coordinated water in the Eu(III)-based chelate. According to the ratiometric method on which the method of the invention is based, the CEST effect evaluated as $[(M_0-M_S)/M_S]_{YbL}/[(M_0-M_S)/M_S]_{EuL}$ ratio is not dependent on the absolute concentration of the contrast agents but only on their relative concentration ratio. On this basis, the pH dependence of the $[(M_0-M_S)/M_S]_{YbL}/[(M_0-M_S)/M_S]_{EuL}$ ratio was investigated at 7.05 T, 312 K on a solution containing 16 mM of Eu-DOTAM-Gly and 20 mM of the Yb(III)-based chelate (irradiation time 4 s, irradiation power 25 µT). The result reported in FIG. 9 shows the high responsiveness to the pH of the system of the invention. Interestingly, the marked pH dependence observed for such system, which ensures a good sensitivity to the method, is basically due to the pH dependence of the ST effect shown by the Yb(III) chelate. In fact, the ST effect arising from the irradiation of the protons of the coordinated water in the Eu-DOTAM-Gly complex is basically unaffected in the investigated pH range from 5.5 to 8.5 (FIG. 10). This allows the full exploitation of the pH dependence of the Yb(III) chelate which results in a remarkable pH dependence of the ST ratio in pH range from 6.5 to 8.1 considerably larger than the one reported by Balaban and Ward in their diamagnetic system (Ward K M and Balaban R S. Magn Res Med 2000; 44: 799-802).

In another experiment we have checked the validity of one of the preferred method of the invention for the pH determination in vitro when a single paramagnetic complex endowed with two magnetically non equivalent pools of mobile protons is used. In FIG. 11 the pH dependence of the ratiometric plot (amide protons over coordinated water protons) for a 30 mM solution of Eu-DOTAM-Gly at 312° K and 7.05 T is reported.

The experiment has been carried out by irradiating the two pools of mobile protons for 2 seconds with the same modality of irradiation (selective e-burp pulses) reported above for this complex.

The data reported in FIG. 11 suggest that the pH dependence is maintained, even if the sensitivity of this method is quite significantly reduced with respect to the data reported in FIG. 9. The reason is mainly due to the lower efficiency of the ST effect for the amide protons of Eu(III)-DOTAM-Gly complex.

The pH dependence of the ST effect has been also assessed for the [Yb—Eu(bisDOTAM-Gly)] derivative (30 mM, 312 K, irradiation power 25 µT, irradiation time 4 s) and the result, under the form of the ratiometric plot (amide protons of Yb(III) versus metal bound water protons of Eu(III)), is showed in FIG. 12. The sensitivity of the ratiometric plot to the pH of the solution for the dimer is lower than the mixture of Eu(III) and Yb(III)-DOTAMGly (FIG. 9). It is likely that this difference is due to the lower $K^{conc}$ value (1 vs 1.25) for the dimer. Nevertheless, the sensitivity of the dimer is higher than that one observed when the single Eu(III)-DOTAMGly complex (FIG. 11) is used.

Temperature Responsive CEST Agents

The exchange rate of any mobile proton is temperature dependent.

The temperature can also affect the chemical shift value of the exchanging protons induced by the paramagnetic metal and the $T_1$ value of the water signal. On this basis, any paramagnetic complex whose chelating ligand includes at least a mobile proton can advantageously be used as temperature responsive CEST agent according to the method of the invention.

In the case of mixed valence compounds (D. E. Richardson and H. Taube in Coord. Chem. Rev. 1984, 60:107-129), the change of the electron spin configuration caused by a temperature variation can also be exploited for the attainment of a very efficient temperature responsive CEST agent according to the method of the invention.

The responsiveness to the temperature according to the method of the invention has been tested for the Eu-DOTAM-hydrazide complex compound (30 mM; pH 7.4). The temperature dependence of the saturation transfer has been tested by irradiating the mobile water protons coordinated to the metal centre. The result is reported in FIG. 13. The responsiveness to the temperature according to the method of the invention has been tested also by use of a composition containing Tm(III)-DOTAM-Gly together with the Eu(III) complex of the same ligand. Upon irradiation of the amide protons of the Tm(III)-DOTAM-Gly and the water protons metal coordinated to the Eu(III)-complex, according to the method of the invention, a satisfactory results has been obtained, as shown in FIG. 13 Bis.

CEST Agents Responsive to the Concentration of Metabolites

In order to be responsive to a specific metabolite, a paramagnetic CEST agent has to be able to interact non covalently and as selectively as possible with it and this interaction must promote changes in the parameters determining the saturation transfer efficacy such as, for example, chemical shift, exchange rate, relaxation rate of bulk water, number of mobile protons.

The responsiveness to a given metabolite according to a preferred method of the invention has been tested in vitro by using the Yb(III) complex of the heptadentate 10-[(3-methoxyphenyl)methyl]-1,4,7,10-tetraazaciclododecane-1,4,7-tris-[(aminocarbonyl)methyl] chelating ligand (Ligand G). The chelating ligand of this paramagnetic complex has been prepared as disclosed in the European patent Application 01124440.7. This chelate owns 6 mobile amide protons whose chemical shift separation from the bulk water is ca 29 ppm upfield the bulk water signal at 312° K. This complex is able to interact quite strongly with several anionic substrate endowed with coordinating groups able to replace the water molecules coordinated to the metal centre of the chelate complex.

Among the anionic substrates of interest for this application, one may include both endogenous and exogenous compounds.

More preferably, the endogenous substrates are selected from the group consisting of lactate, citrate, carbonate, phosphate, pyruvate, natural amino-acids, oxalate, tartrate, succinate, choline, creatine, acetate, and malonate.

Even more preferably, the substrates are human metabolites, wherein lactate, citrate, carbonate, and phosphate are the most preferred.

Moreover, the substrate molecule of interest for the method of the invention can be an exogenous substance, wherein the term exogenous, as used herein, refers to any substance of pharmacological or diagnostic interest, eventually modified in order to allow a suitable binding to the paramagnetic complex.

As a representative, but not limiting, example we have considered L-lactate.

The affinity constant between the metal complex and L-lactate has been evaluated through relaxometric measurements carried out on the Gd(III) complex ($K_A$ of ca. 3000 at 298° K and pH 6.5). The exchange between the free and the lactate-bound Yb(III) complex is slow on the NMR frequency timescale. Therefore, different resonances for the mobile amide protons for the two forms ($\Delta\omega$ of 29 ppm and 15 ppm for the free- and bound-forms, respectively) of the metal complex may be detected at physiological conditions (312° K and pH 7.4) in the $^1$H-NMR spectrum.

The signals corresponding to the two forms of the CEST agent are sufficiently separated to allow their selective irradiation. The dependence on the L-lactate concentration of the ST effect promoted by the irradiation of the free amide protons in a 9.3 mM solution of Yb(III) complex of the heptadentate 10-[(3-methoxyphenyl)methyl]-1,4,7,10-tetraazaciclododecane-1,4,7-tris-[(aminocarbonyl)methyl] chelating ligand is shown in FIG. 14 (7.05 T, pH 7.4, 312 K, irr. power 1050 Hz, irr. time 6 s).

Interestingly, the ST efficiency shows a marked dependence in the range of Lactate concentration (0-10 mM) of diagnostic relevance.

This result has been confirmed by recording a PDW $^1$H-MR image (298 K, pH 7.4, 7.05 T) of a phantom consisting of solutions at different concentrations of L-lactate in the 0-10 mM range (FIG. 15).

The independence of the ST effect on the concentration of the CEST agent can be achieved, according to this invention, by use, for example, of a dimeric complex compound comprising Yb-G and Eu-DOTAM-Gly units.

CEST Agents Responsive to the Partial Pressure of $O_2$

The Co(II) high spin chelated complex of the ligand G represent an example of a paramagnetic CEST agent responsive to partial pressure of the $O_2$ for use in the method of the invention.

According to the following scheme:

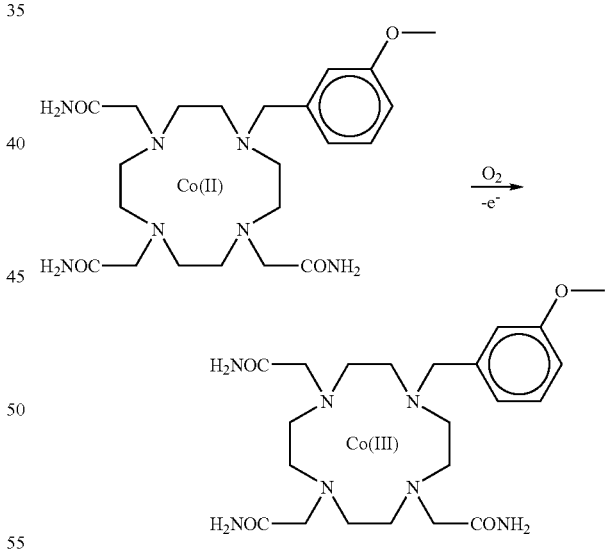

$O_2$ can transform the Co(II)-high spin complex into the Co(III)-low spin diamagnetic complex wherein this results in a considerable reduction of the CEST effect upon irradiation of the exchangeable amide protons coordinated to the metal centre of the complex compound.

As another example of CEST agents responsive to the redox potential of the medium, Ln(III) complexes of Ligand L have been prepared.

These ligands contains a diphenylamine substituent which act as a redox-switch whose redox potential is very close to that one present in vivo (ca. 0.8 V).

A third example of CEST agents sensitive to the partial pressure of $O_2$ is represented by the Co complex of Ligand M. Analogously to the Co-G complex, the responsiveness of this system is due to the redox equilibrium between the paramagnetic high spin Co(II) form and the diamagnetic low-spin Co(III) compound. Unlike from the other examples, here the ST effect is measured upon irradiation of the amine protons of the complexes.

The dependence of the ST effect on the partial pressure of $O_2$ can be observed upon irradiating of either the frequency resonance of the metal bound water protons in the Eu(III) complex or the amide protons of the other Ln(III) chelates. The concentration independence of the ST effect can be obtained, according to this invention, by using a single complex (Eu(III)-L chelate), a mixture of Eu(III)-L and Yb(III)-L compounds or by using a dimer constituted by the redox-sensitive unit (e.g. Yb(III)-L, Co-G or Co-M complexes) linked to a DOTAM-Gly unit containing Eu(III) ion.

BRIEF DESCRIPTION OF THE DRAWINGS

FIG. 6: pH dependence of the saturation transfer effect for a 20 mM solution of Yb-ligand G ($B_0$=7.05 T, 312 K, irradiation power 25 µT, irradiation time 4 s).

FIG. 6 Bis: pH dependence of the saturation transfer effect for a 30 mM solution of Yb-DOTAM-Gly ($B_0$=7.05 T, 312 K, irradiation power 25 µT, irradiation time 4 s).

FIG. 13: Temperature dependence resulting by the irradiation of the mobile water protons coordinated to Eu-DOTAM-hydrazide (30 mM; pH 7.4, $B_0$=7.05 T, 312 K, irradiation time 2 s, irradiation power 15.7 µT).

FIG. 13 Bis: Temperature dependence resulting by the exploitation of the ratiometric method (Eu-DOTAM-Gly=14 mM; Tm-DOTAM-Gly=14 mM; 7.05 T, pH 7.4, irradiation time 4 s, irradiation power 25 µT).

EXPERIMENTAL SECTION

Figure 1:
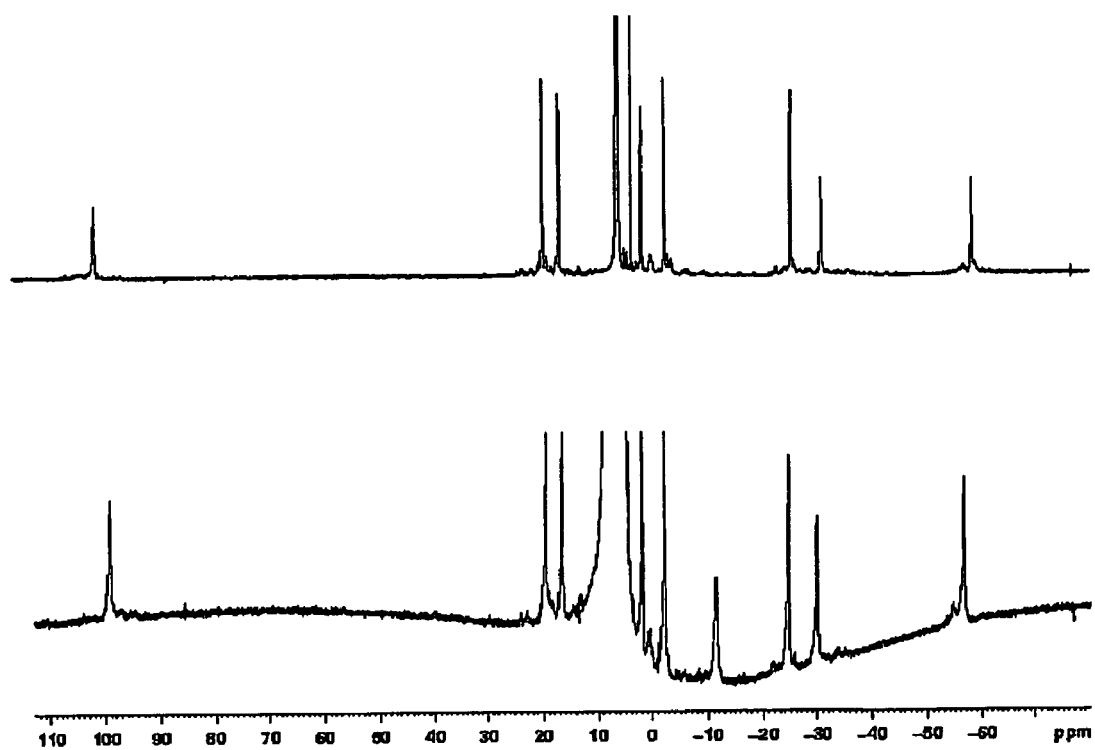
FIG. 1: $^1$H-NMR spectra of Yb-DOTAM-Gly (7.05 T, 298 K and pH 7) in $D_2O$ (top) and $H_2O$ (bottom).
Figure 2:
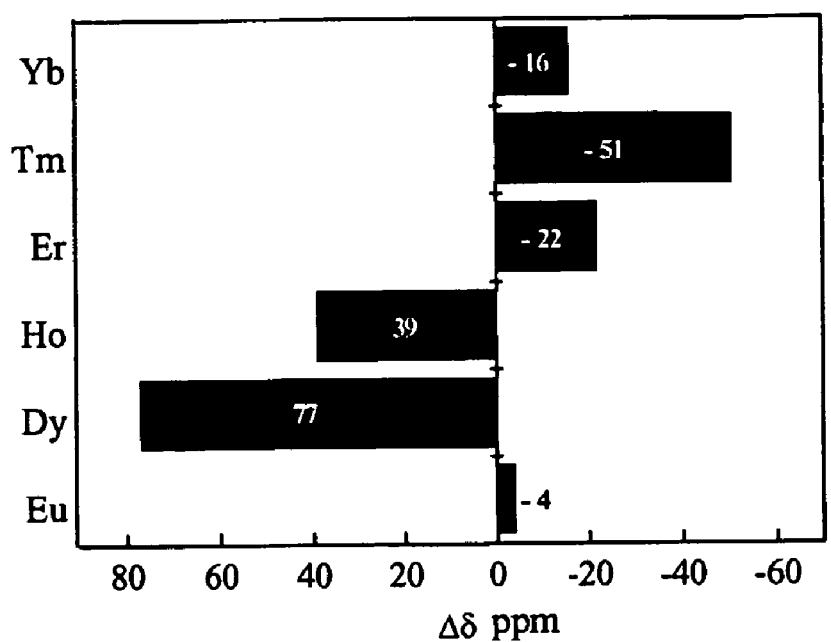
FIG. 2: Chemical shift difference ($\Delta\omega$ in ppm) between the amide N—H protons and bulk water for Ln-DOTAM-Gly chelates. (7.05 T, 312 K)
Figure 3:
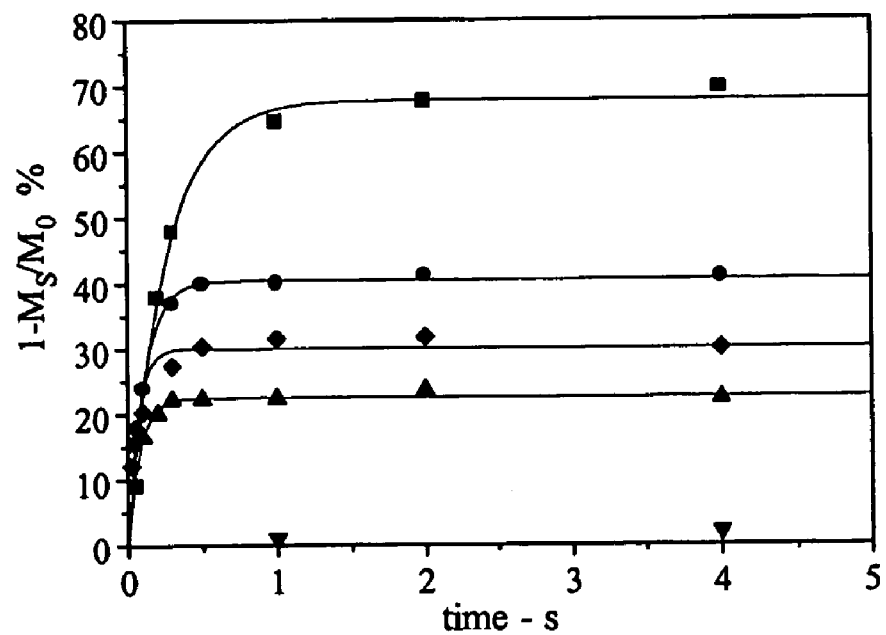
FIG. 3: Dependence of the saturation transfer on the irradiation time (irradiation power 25 µT) for Dy-(30 mM, down-triangle), Ho-(30 mM, up-triangle), Er-(40 mM, diamond), Tm-(40 mM, circle) and Yb-(30 mM, square) chelates of DOTAM-Gly ($B_0$=7.05 T, 312 K, pH 8.1).
Figure 4:
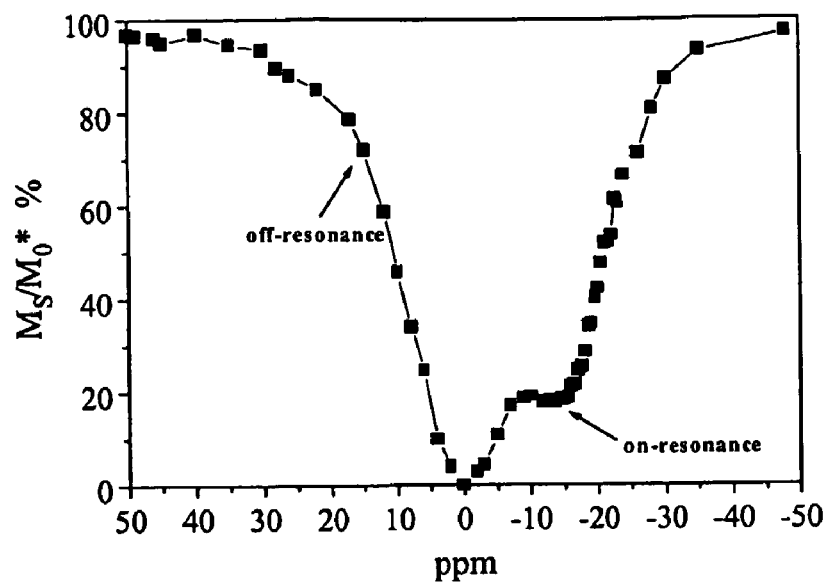
FIG. 4: CEST spectrum of a 30 mM solution of Yb-DOTAM-Gly at pH 8.1 ($B_0$=7.05 T, 312 K, irradiation time 4 s, irradiation power 25 µT).
Figure 5:
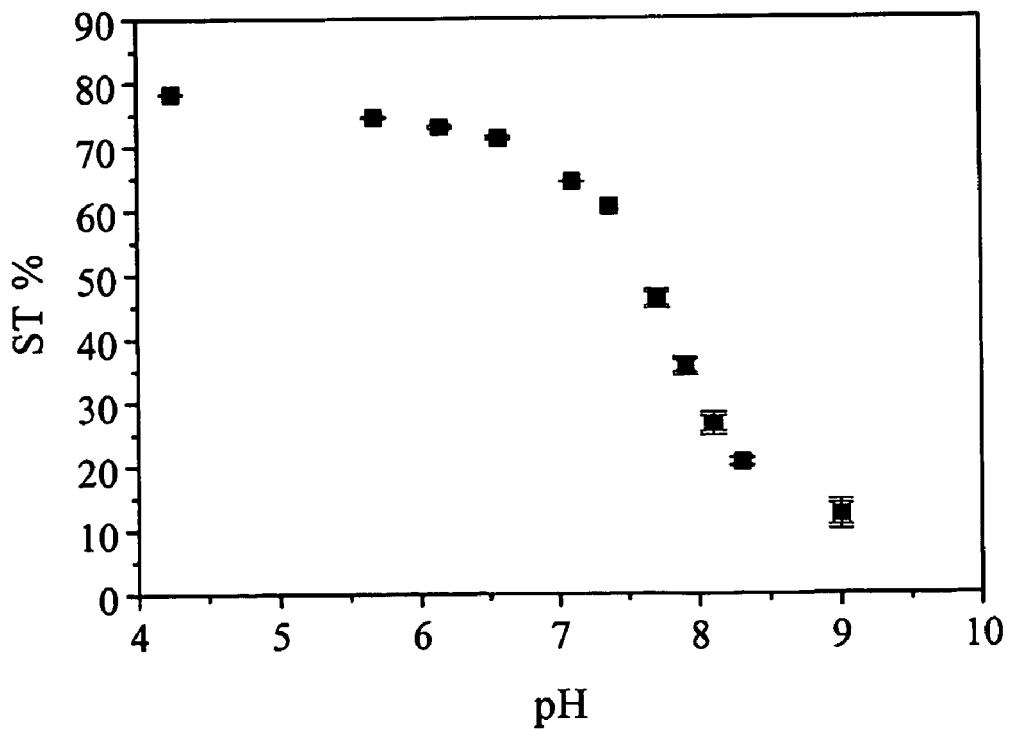
FIG. 5: pH dependence resulting by the irradiation of the mobile water protons coordinated to Eu-DOTAM-hydrazide (30 mM; pH 7.4, $B_0$=7.05 T, 312 K, irradiation time 2 s, irradiation power 15.7 µT).
Figure 7:
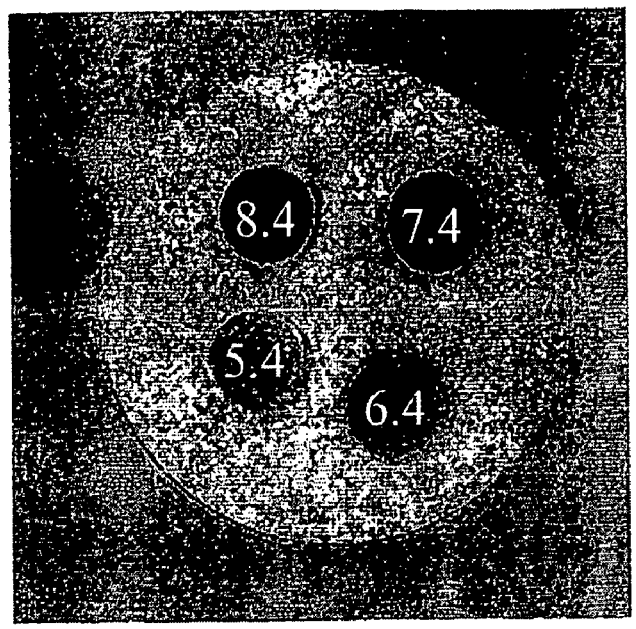
FIG. 7: 7.05 T PDW Spin-echo image of a phantom containing 4 vials of Yb-DOTAM-Gly (30 mM) in the pH range 5.4-8.4. The vials were dipped in water containing 30 mM of Yb(III) aqua-ion (298 K, irradiation time 4 s). The image is the difference between two PDW images (TR=3.04 s; TE=18.3 ms) in which the pre-saturation pulse was centred first on the amide protons (−4794 Hz from bulk water) and then symmetrically off-resonance (4794 Hz from bulk water).
Figure 8:
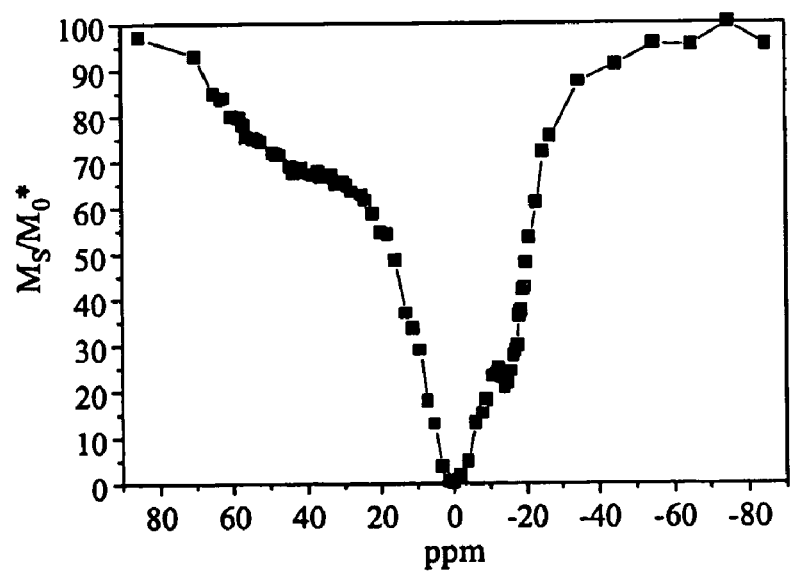
FIG. 8: CEST spectra of a solution containing 16 mM of Eu-DOTAM-Gly and 20 mM of Yb-DOTAM-Gly at pH 8.1 ($B_0$=7.05 T, 312 K, irradiation time 4 s, irradiation power 25 µT).
Figure 9:
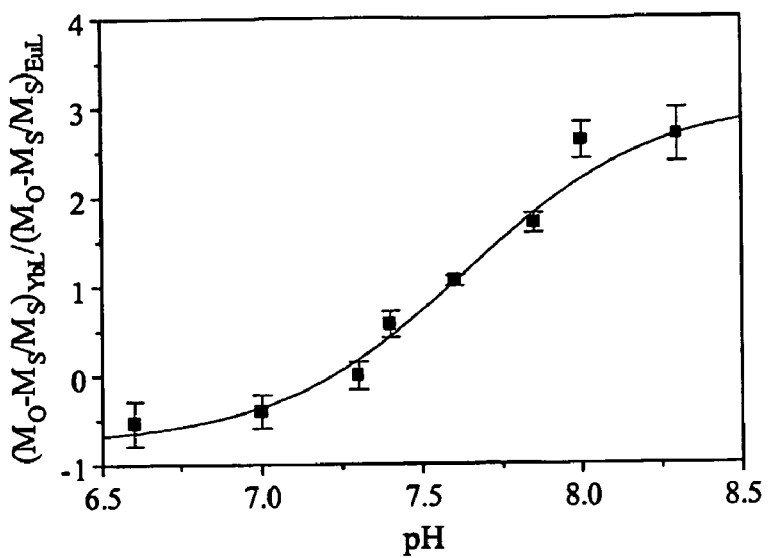
FIG. 9: pH dependence resulting by the exploitation of the ratiometric method (Eu-DOTAM-Gly concentration 10 mM, Yb-DOTAM-Gly concentration 12.5 mM; 7.05 T, 312 K, irradiation time 4 s, irradiation power 25 µT). The error bars indicate the standard deviation of 5 independent measurements.
Figure 10:
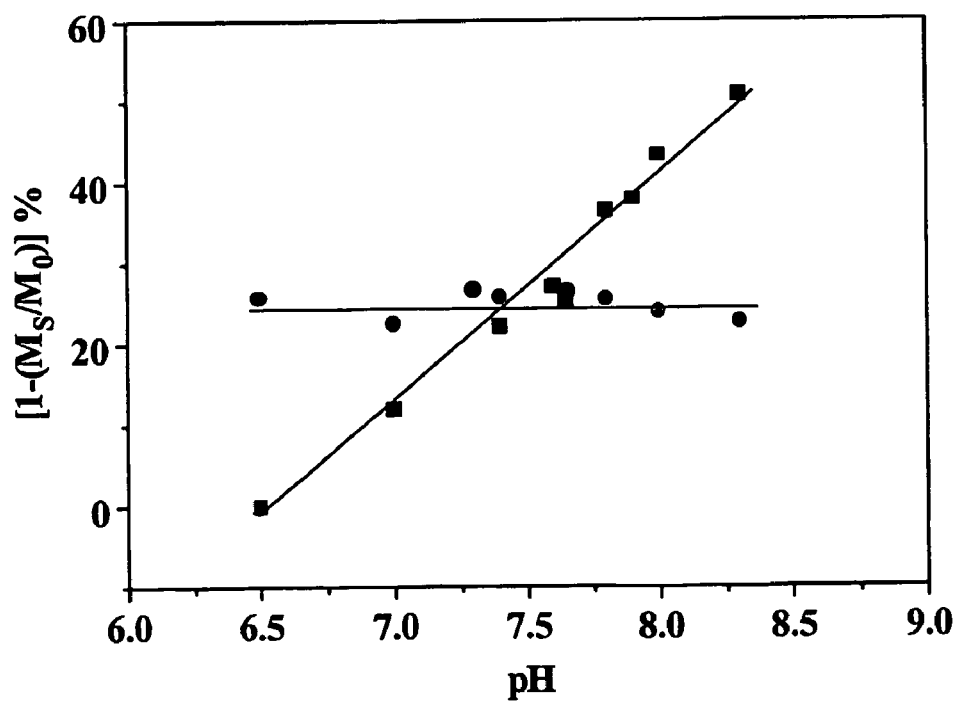
FIG. 10: pH dependence of ST effect for a solution containing 10 mM of Eu-DOTAM-Gly and 12.5 mM of Yb-DOTAM-Gly (7.05 T, 312 K, irradiation time 4 s, irradiation power 25 µT). The square refer to the irradiation of the amide protons of the Yb(III) complex and the circle correspond to the irradiation of the coordinated water protons in the Eu(III) chelate.
Figure 11:
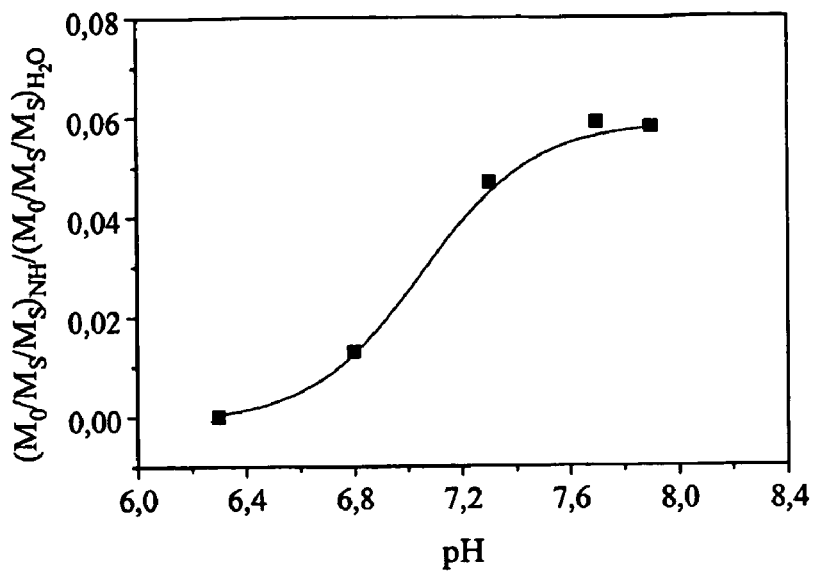
FIG. 11: pH dependence resulting by the exploitation of the ratiometric method of a 30 mM solution of Eu-DOTAM-Gly (7.05 T, 312 K, irradiation time 2 s). The saturation has been performed by using a train of 270° e-burp1 pulse (20 ms each, power 1.2 µT) for the amide protons and a train of 90° e-burp1 pulse (1 ms each, power 15.7 µT) for the metal bound water protons.
Figure 12:
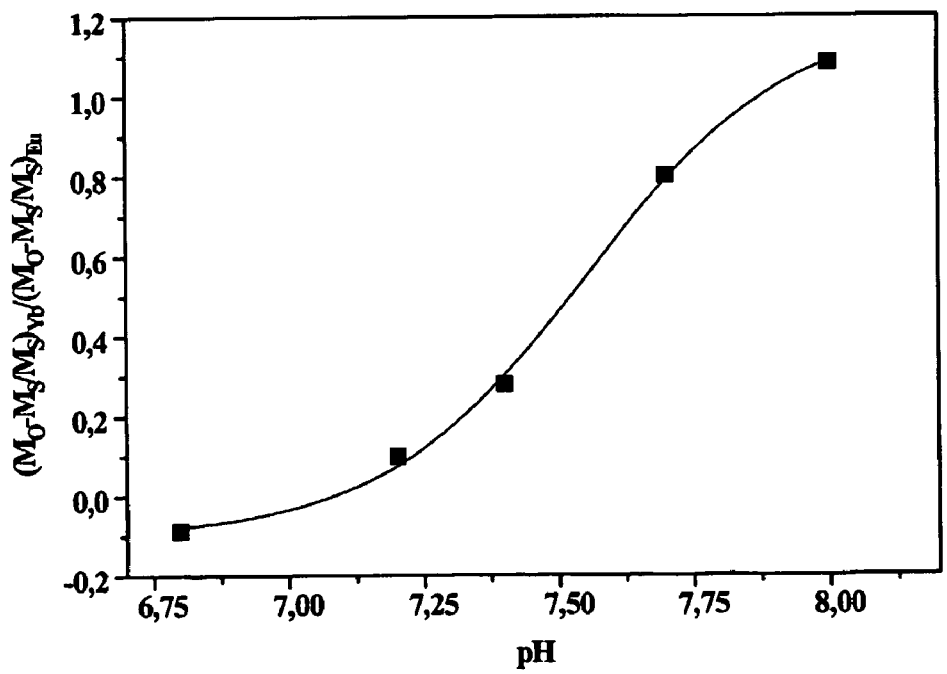
FIG. 12: pH dependence resulting by the exploitation of the ratiometric method for the Yb—Eu-bisDOTAM-Gly dimer (agent concentration 30 mM, $B_0$=7.05 T, 312 K, irradiation time 4 s, irradiation power 25 µT).
Figure 14:
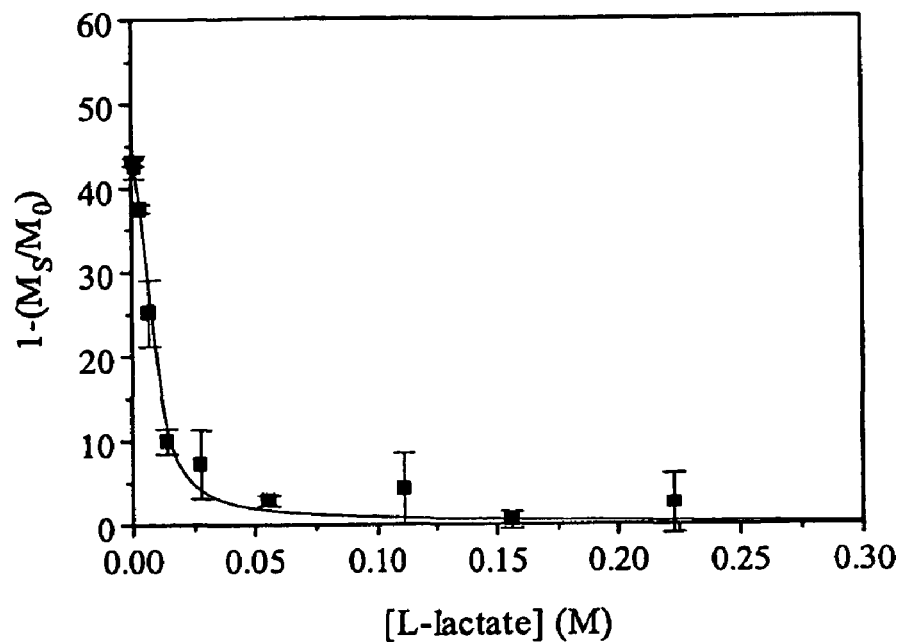
FIG. 14: Dependence on the L-lactate concentration of the ST effect of a 9.3 mM solution of Yb(III) complex of the 10-[(3-methoxyphenyl)methyl]-1,4,7,10-tetraazaciclododecane-1,4,7-tris-[(aminocarbonyl)methyl] chelating ligand measured by irradiating the amide protons of the free chelate at −29 ppm from the bulk water protons (7.05 T, 312 K, pH 7.4, irr. time 4 s, irr. power 1050 Hz).
Figure 15:
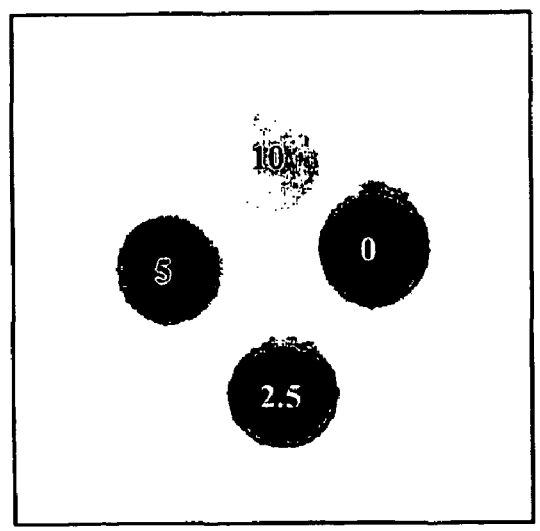
FIG. 15: 7.05 T PDW Spin-echo image of a phantom containing 4 vials of Yb-Ligand G (9.3 mM) containing different L-lactate concentrations in the 0-10 mM range. The image is the difference between two PDW images in which the saturation pulse was centred first on the amide protons of the free complex (−8700 Hz from bulk water) and then symmetrically off-resonance (8700 Hz from bulk water).

The preparation of the compounds of the invention has been performed according to procedures and synthesis steps well known to a man skilled in the art. Non limiting examples are included below.

Preparation of
1,4,7,10-tetraazaciclododecane-1,4,7,10-acetic acid
tetraglycineamide (DOTAM-Gly)

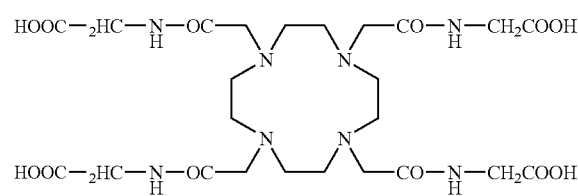

The chelating ligand was synthesized according to the following steps:

a) exhaustive alkylation of TAZA (TAZA=1,3,5,7-tetraaza-cyclododecane, 0.075 mol) with N-(2-Bromoethanoyl) ethyl glycinate (0.3 mol) in the presence of 0.3 mol of $K_2CO_3$ as base to give the corresponding tetraethyl ester derivative.

The reaction was carried out in acetonitrile by heating at 70° C. for 6 h. After removal of the undissolved materials by filtration, the product was simply obtained by evaporating the solvent. Yield: 91.4%

N-(2-Bromoethanoyl) ethyl glycinate was syntetisized according to the published procedure. (Kataki R, et al. J Chem Soc Perkin Trans 2 1992; 8:1347-1351).

b) controlled saponification of the tetraethyl ester and isolation of the desired tetracarboxylic acid.

The saponification of the tetraester was carried out in 200 mL of ethanol/water (1:1) solution at 60° C. NaOH 1 N (232 mL) was added to maintain the pH of the solution constant (pH 11) for almost 45'. The reaction was complete after 1 h heating. The resulting orange solution was cooled down and acidified at pH 2.2 with HCl. The DOTAM-Gly ligand was separated from such solution by liquid chromatography (solid-phase: Amberlite® XAD-1600; eluent: water). Yield: 88%. The ligand has been characterized by MALDI-TOF Mass Spectrometry (calc. for $C_{32}H_{40}N_8O_{12}$, 632.63 amu; found 633.55 (MH+)).

Synthesis of the Ln(III) Complexes

The Ln(III)-DOTAM-Gly complexes were prepared by mixing equimolar amount (0.3 mmol) of the ligand and the corresponding Ln(III) chloride in 10 mL of water (room temperature, pH 8, 30'). The recovered chelate complexes have been characterized by means of their $^1$H-NMR spectra. The recovered data were consistent with the expected structures.

Preparation of the Ligand B (DOTAM-Gly)

The synthesis has been carried out through the following steps:

Synthesis of N-(Benzyl-oxy carbonyl)-N'-(bromoacetyl) hydrazine (dichloro-methane, 0° C.)

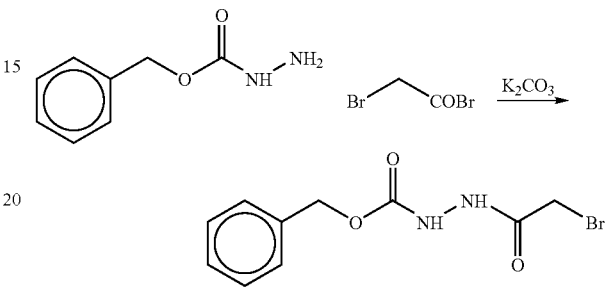

Synthesis of 1,4,7,10-tetra{2-[N'-(benzyl-oxy-carbonyl) hydrazino]-2-oxo-ethyl}-1,4,7,10-tetraazacyclododecane (acetonitrile, room temperature):

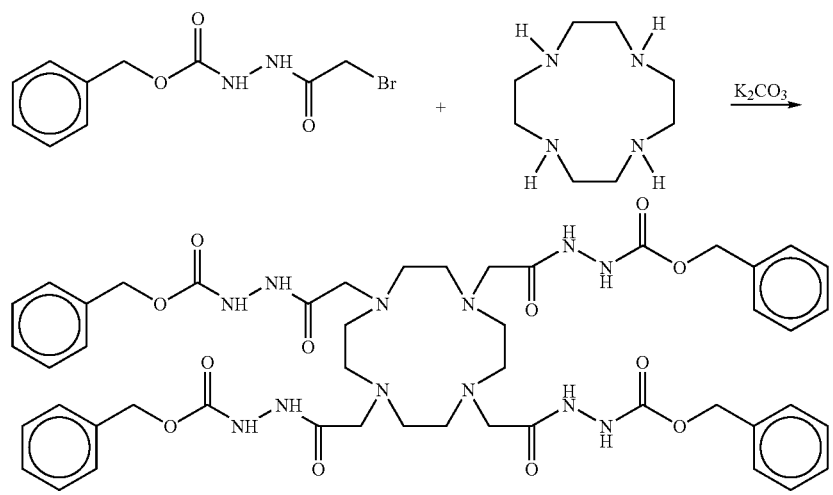

Synthesis of ligand B (methanol, room temperature)

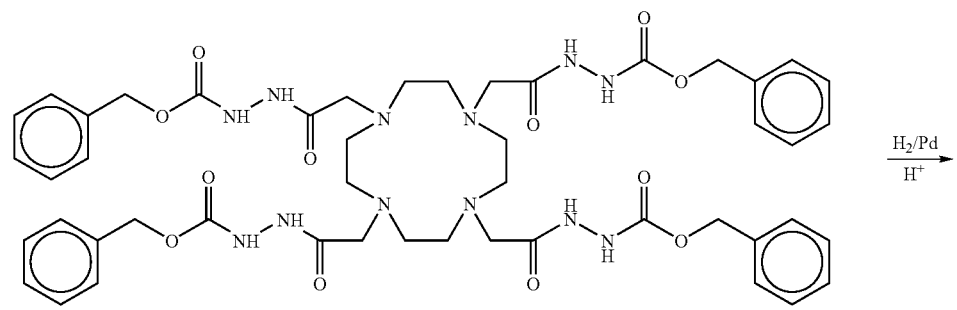

-continued

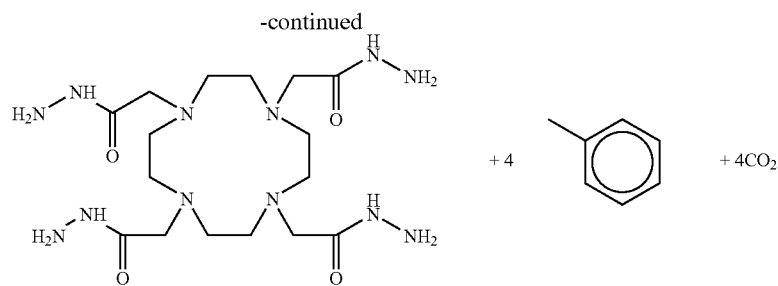

Preparation of the Ligand C

Main steps include:

Synthesis of 1-(4-nitrophenyl)-1,4,7,10-tetraazacyclododecane (acetonitrile/water 10:1, 60° C.)

Synthesis of 1-(4-nitrophenyl)-1,4,7,10-tetraazacyclododecane-1,4,7-tris-acetamide (acetonitrile, room temperature)

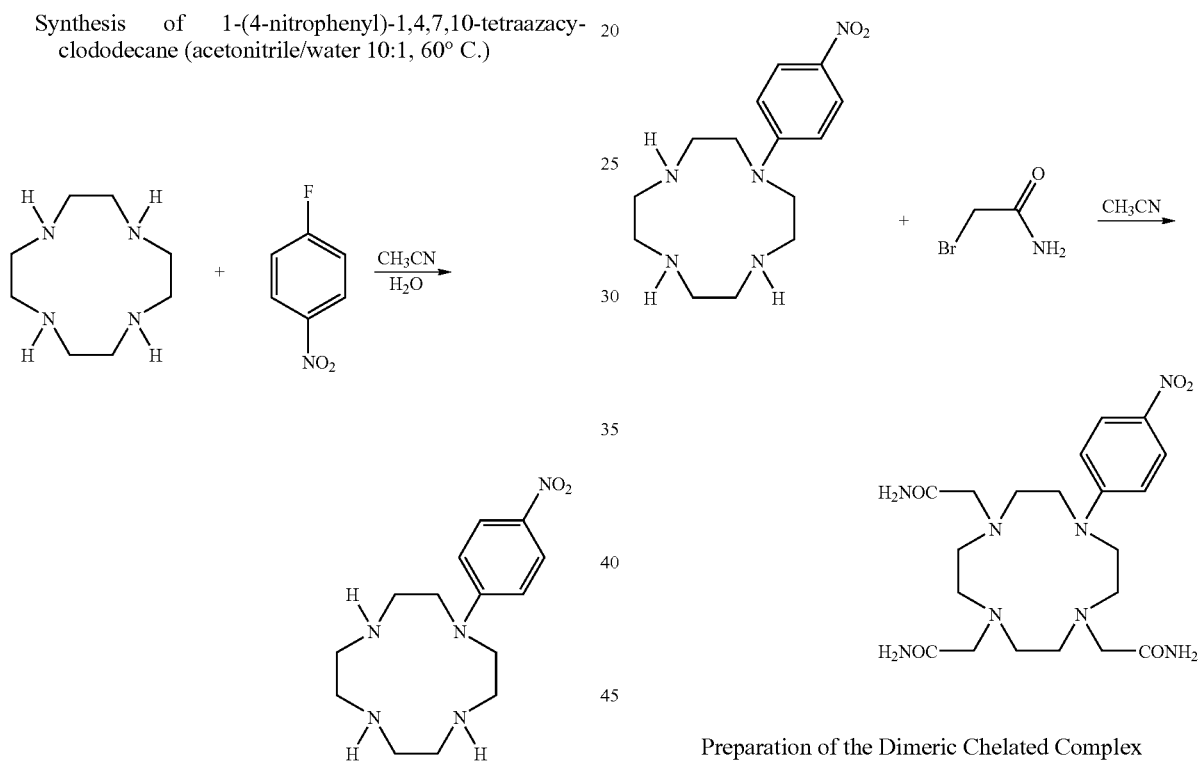

Preparation of the Dimeric Chelated Complex [Eu—Yb(bisDOTAMGLy)]

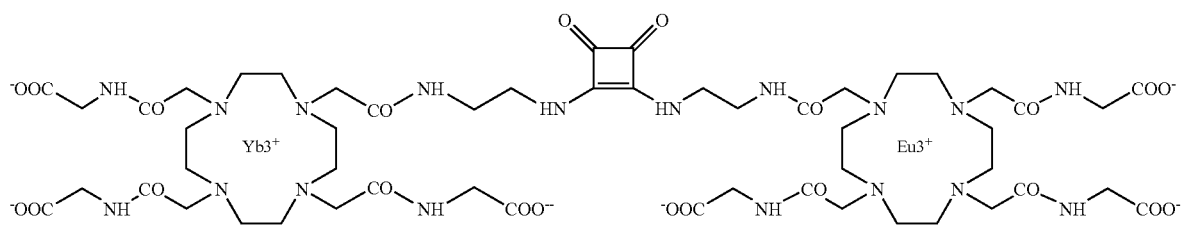

The global preparation has been performed according to a procedure schematized below:

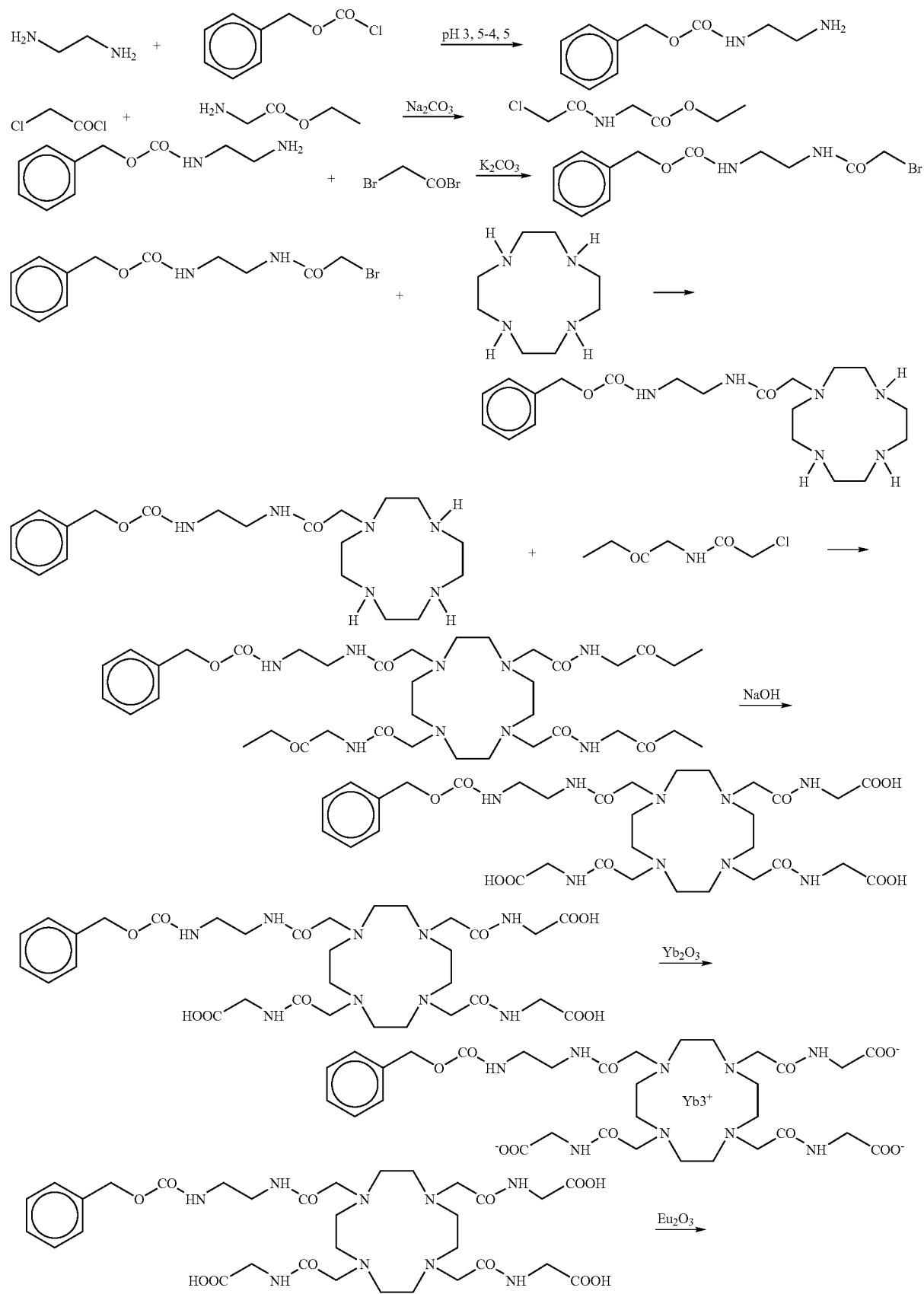

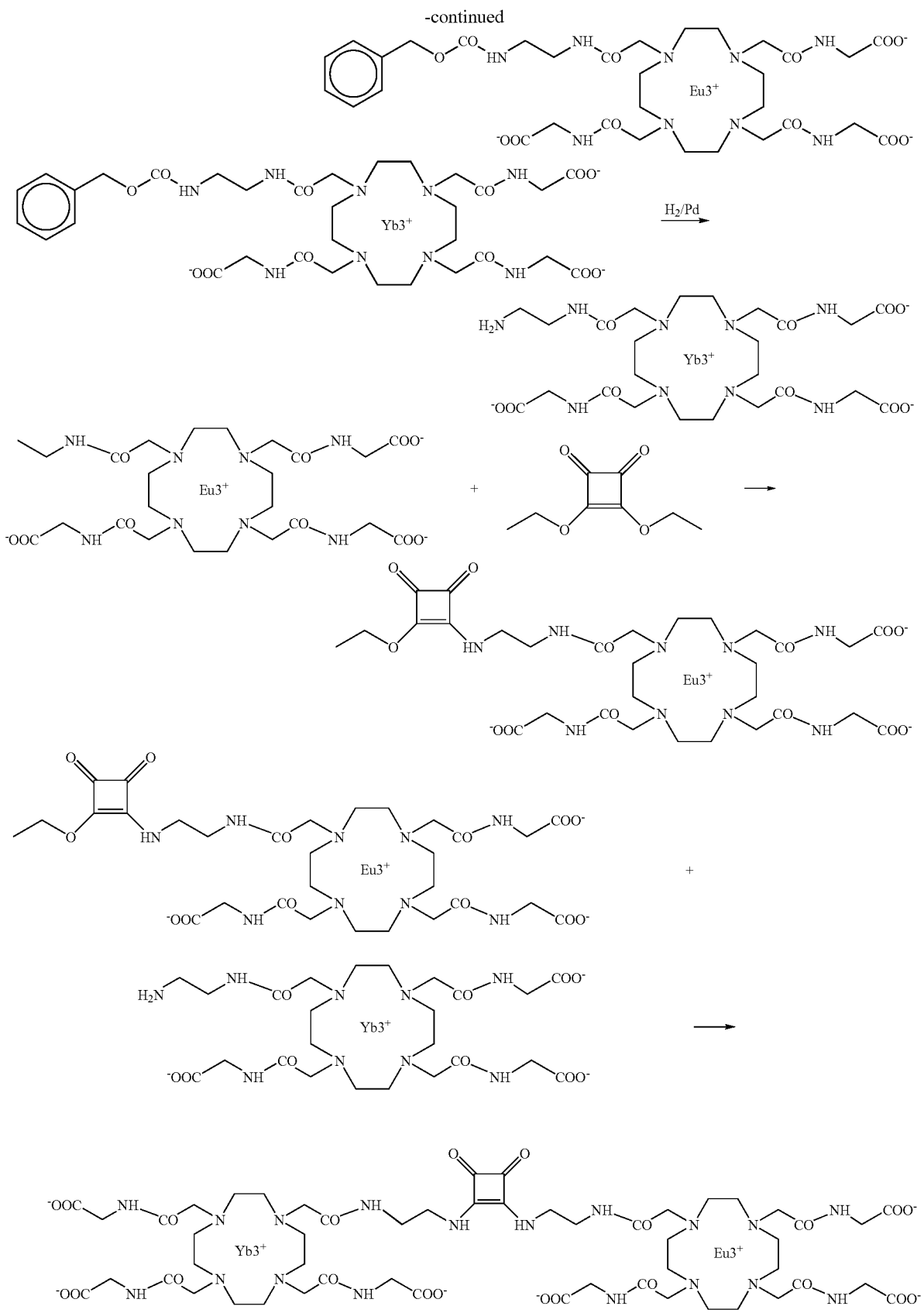

Those skilled in the art should realize that, by use of the above scheme and by suitably changing the chelating unit or the chelated metal ion any dimeric contrast agent according to the method of the invention can be easily obtained.

NMR Methods

The high resolution work has been carried out on a Bruker Avance 300 spectrometer operating at 7.05 T.

The saturation transfer experiments were carried out at 312° K by irradiating the sample with a continuous wave presaturation square pulse (power of 1050 Hz) or by using a proper train of e-burp1 selective pulses. Four scans and 4 dummy scans were used for all the experiments.

NMR imaging was performed using a 7.05 T Bruker PharmaScan having actively shielded gradients 300 mT/m) and running ParaVison 2.1.1 software. Standard PDW (proton density weighted images) were obtained using a SE (spin-echo) imaging sequence (using Hermite shaped 90° and 180° pulses). NMR image adopted parameters were (TR/TE/NE=3.0 s/18.3 ms/1); FOV (Field Of View) 30×30 mm$^2$; slice thickness 2 mm and image matrix 256×256 points. A 2.25 Watt square shaped saturation pulse was applied for 4 s in the pre-delay of the spin-echo sequence. Two images were acquired, one with saturation of the amide protons at −4794 Hz from bulk water protons and the other with the rf irradiation offset at 4794 Hz.

The invention claimed is:

1. A method for the determination, by use of the CEST MRI technique, of a physical or chemical parameter selected from temperature, pH, metabolite concentration, $O_2$ or $CO_2$ partial pressure and enzymatic activity in a human or animal body organ, fluid or tissue, wherein:

a responsive paramagnetic CEST contrast agent is administered comprising at least one exchangeable proton whose saturation capability is correlated to the physical or chemical parameter of interest, and a CEST MR image responsive for said parameter is generated, the employed CEST contrast agent comprising a paramagnetic chelate compound in which the chelating ligand is a compound of formula (I)

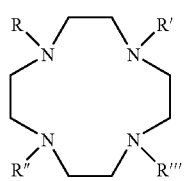

(I)

where:

| | |
|---|---|
| R = R' = R" = R'" = —CH$_2$—CONH—CH$_2$COOH | Ligand A |
| R = R' = R" = R'" = —CH$_2$—CONHNH$_2$ | Ligand B |
| R = R' = R" = —CH$_2$—CONH$_2$ 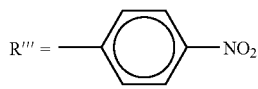 | Ligand C |
| R = R' = R" = —CH$_2$—CONH$_2$ 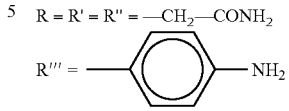 | Ligand D |
| R = R' = R" = —CH$_2$—CONH$_2$ 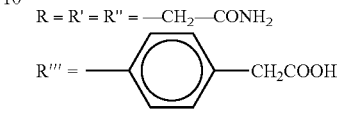 | Ligand E |
| R = R' = R" = —CH$_2$—CONH—CH$_2$—COOBu 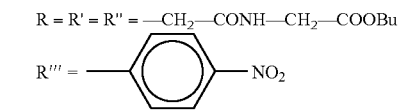 | Ligand F |
| R = R' = R" = —CH$_2$—CONH$_2$ 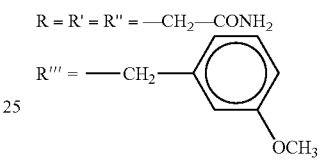 | Ligand G |
| R = R' = R" = —CH$_2$—CONH$_2$ 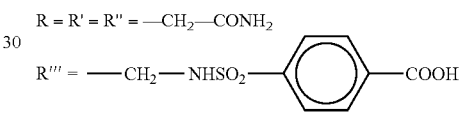 | Ligand H |
| R = R' = R" = —CH$_2$—CONH—CH$_2$COOH 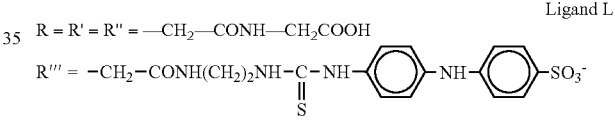 | Ligand L | and the paramagnetic ion is selected from the group consisting of iron (II) (high spin), iron (III), cobalt (II), copper (II), nickel (II), praseodymium (III), neodymium (III), dysprosium (III), erbium (III), terbium (III), holmium (III), thulium (III), ytterbium (III), and europium (III), or a physiological acceptable salt thereof.

2. The method of claim 1 wherein the CEST contrast agent comprises at least two magnetically non equivalent pools of mobile protons.

3. The method of claim 1 in which the determination is performed in vitro or ex vivo.

4. The method of claim 2 wherein the determination is performed in vivo.

5. The method of claim 1 wherein the paramagnetic chelate complex comprises a water molecule coordinated to the paramagnetic centre.

6. The method of claim 5 wherein the mobile proton in the CEST contrast agent either belong to an amide group of the chelating ligand or is a metal bound water proton of said paramagnetic chelate complex.

7. The method of claim 2 wherein the CEST contrast agent comprises a single paramagnetic complex compound endowed with two magnetically non equivalent pools of mobile protons or a physiologically acceptable salt thereof.

8. The method of claim 2 wherein the CEST contrast agent comprises two paramagnetic complex compounds which have the same biodistribution pattern, each of them providing a different pool of mobile protons.

9. The method of claim 7 wherein one of the two magnetically non equivalent pools of mobile protons belongs to an amide group of the chelating ligand and the second belongs to a metal coordinated water molecule.

10. The method of claim 8 wherein the CEST contrast agent comprises Eu(III) DOTAM-Gly together with Yb(III) DOTAM-Gly or Tm(III)-DOTAM-Gly, or a physiologically acceptable salt thereof.

11. A pharmaceutical composition which includes, together with a physiologically tolerable carrier, Eu(III)-DOTAM-Gly together with Yb-DOTAM-Gly or Tm-DOTAM-Gly, or a physiologically acceptable salt thereof in a molar ratio ranging from 1 to 30.

12. The pharmaceutical composition of claim 11 wherein the two paramagnetic complexes are in a molar ratio ranging from 1 to 5.

13. A compound selected among:
DOTAM-hydrazide; a chelate complex of DOTAM-hydrazide with a paramagnetic metal ion selected from the group consisting of: iron (II) (high spin), iron (III), cobalt (II), copper (II), nickel (II), praseodymium (III), neodimium (III), dysprosium (III), erbium (III), terbium (III), holmium (III), thulium (III), ytterbium (III), and europium (III); and their physiologically acceptable salts.

14. The method of claim 1 wherein $R=R'=R''=R'''=$—$CH_2$—CONH—$CH_2$COOH.

* * * * *